United States Patent [19]

Adamczyk et al.

[11] Patent Number: 5,578,500

[45] Date of Patent: Nov. 26, 1996

[54] REAGENTS AND METHODS FOR THE QUANTIFICATION OF IMIPRAMINE OR DESIPRAMINE IN BIOLOGICAL FLUIDS

[75] Inventors: Maciej Adamczyk, Gurnee; Charles A. Harrington, Lake Villa; Donald Johnson, Lindenhurst, all of Ill.

[73] Assignee: Abbott Laboratories, Abbott Park, Ill.

[21] Appl. No.: 286,731

[22] Filed: Aug. 5, 1994

Related U.S. Application Data

[60] Division of Ser. No. 916,161, Jul. 24, 1992, Pat. No. 5,340,750, which is a continuation-in-part of Ser. No. 739,012, Jul. 31, 1991, abandoned.

[51] Int. Cl.$^6$ .......................... G01N 33/542; C12N 9/96; C07K 16/44; C07D 223/18
[52] U.S. Cl. .................. 436/537; 435/7.93; 435/188; 436/536; 436/544; 436/546; 530/389.8; 530/404; 530/807; 540/592
[58] Field of Search .................................. 435/7.93, 188; 436/536, 537, 544, 545, 546, 815; 530/389.8, 807, 404; 540/592

[56] References Cited

U.S. PATENT DOCUMENTS

| | | | |
|---|---|---|---|
| 4,223,013 | 9/1980 | Hu et al. | 424/85 |
| 4,275,160 | 6/1981 | Singh et al. | 435/188 |
| 4,420,568 | 12/1983 | Wang et al. | 436/536 |
| 4,495,281 | 1/1985 | Buckler et al. | 435/188 |
| 4,551,275 | 11/1985 | Pirio et al. | 435/188 |
| 4,629,691 | 12/1986 | Collins et al. | 435/6 |
| 5,407,835 | 4/1995 | Adamczyk et al. | 436/537 |

FOREIGN PATENT DOCUMENTS 0226730  1/1987  European Pat. Off. .

OTHER PUBLICATIONS

A. Nagy, et al, "Quantitative Determination of Imipramine and Desipramine in Human Blood Plasma by Direct Densitometry of Thin–Layer Chromatograms", J. Pharm. Pharmac., vol. 25, pp. 509–603 (1973).
T. B. Cooper, et al, "A Sensitive GLC Method for the Determination of Imipramine and Desmethylimipramine Using a Nitrogen Detector", Psychopharmacology Communications, vol., 1(4), pp. 445–454 (1975).
J. W. Hubbard, et al, "Radioimmunoassay for Psychotropic Drugs II: Synthesis and Properties of Haptens for Tricyclic Antidepressants", Journal of Pharmaceutical Sciences, vol., 67(11) pp. 1571–1578 (1978).
K. K. Midha, et al, "Monitoring of Therapeutic Concentrations of Psychotropic Drugs in Plasma by Radioimmunoassays", Journal of Analytical Toxicology, vol., 2, pp. 185–192 (1978).
R. Virtanen, "Radioimmunoassay for Tricyclic Anitdepressants", Scand. J. Clin. Lab. Invest., vol., 40, pp. 191–197 (1980).

P. K. Sonsalla, et al, "An Evaluation of the Emit® ST Assay for the Direction of Tricyclic Antidepressant Drugs in Plasma or Serum", Clinical Toxicology, vol., 22(1), pp. 63–76 (1984).
S. Pankey, et al, "Quantitative Homogeneous Enzyme Immunoassays for Amitriptyline, Nortriptyline, Imipramine, and Desipramine", Clin. Chem., vol., 32(5), pp. 768–772 (1986).
Syva, "Practical Considerations for the Evaluation of the Emit® Tricyclic Antidepressant Assays", Emit® Quantitative Tricyclic Antidpressant Assays, pp. 1–13 (1986).
H. Denis, et al, "Enzyme–Linked Immumosorbent Assay for Amitriptyline and Other Antidepressants Using a Monoclonal Antibody", Clinica Chimica Acta, vol., 159, pp. 257–267 (1986).
A. M. O'Callaghan, et al, "Antisera Raised Against the Drug Imipramine", Journal of Neurochemistry, vol., 49(4), pp. 1091–1095 (1987).

(List continued on next page.)

*Primary Examiner*—Mary E. Ceperley
*Attorney, Agent, or Firm*—John F. Levis

[57] ABSTRACT

Immunoassay methods and reagents for the specific quantification of imipramine or desipramine in a test sample are disclosed. The measurement of imipramine or desipramine is accomplished in a specific immunoassay employing antibodies prepared with imipramine or desipramine derivatives of the Formula III:

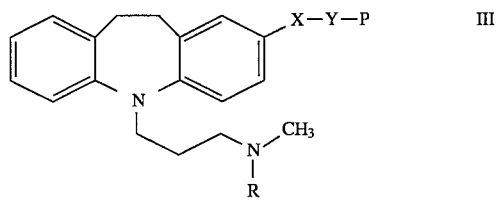

wherein P is an immunogenic carrier material, X is two heteroatoms, Y is a linking group comprising from 1 to 6 carbon atoms and P is an immunogenic carrier material, and wherein for imipramine, R is CH$_3$, and for desipramine, R is H.

The present invention also describes the synthesis of unique labeled reagents of the structure of the Formula IV:

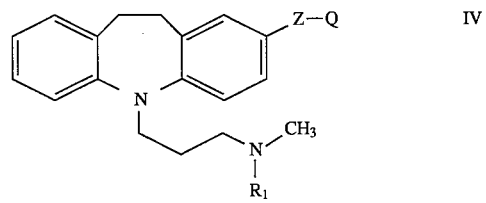

wherein Z is a linking group comprising 1 to 4 carbon atoms and 0 to 2 heteroatoms and Q is a detectable moiety, preferably fluorescein or a fluorescein derivative, and wherein for imipramine, R$_1$ is CH$_3$, and for desipramine, R$_1$ is H.

34 Claims, 14 Drawing Sheets

OTHER PUBLICATIONS

M. Bowles, et al, "Large Scale Production and Purification of Paraquat and Desipramine Monoclonal Antibodies and Their Fab Fragments", Int. J. Immunopharmac., vol., 10(5), pp. 537–545 (1988).

R. Cameron Dorey, et al, "Results Compared for Tricyclic Antidepressants as Assayed by Liquid Chromatography and Enzyme Immunoassay", Clin., Chem., vol., 34(11), pp. 2348–2351 (1988).

D. J. Winzor, et al, "Adaptation of the Muller Method to Allow Quantitative Characterization of the Affinity and Cross–Reactivity of Antibodies by Competitive Radioimmunoassay" Molecular Immunology, vol., 28(9), pp. 995–1001 (1991).

DESIPRAMINE TRACER

Fn = 6-FLUORESCEINYL (SEE ABOVE)

REAGENTS AND METHODS FOR THE QUANTIFICATION OF IMIPRAMINE OR DESIPRAMINE IN BIOLOGICAL FLUIDS

This is a divisional of U.S. Ser. No. 07/916,161, filed on Jul. 24, 1992, now U.S. Pat. No. 5,340,750, which is a continuation-in-part of U.S. Ser. No. 07/739,012, filed Jul. 31, 1991, now abandoned.

FIELD OF THE INVENTION

The present invention relates to the immunoassay quantification of imipramine in a test sample or desipramine in a test sample. In particular, the present invention relates to immunogens, antibodies prepared from such immunogens, and labeled reagents for the specific quantification of imipramine in the presence of its metabolites, and for the specific quantification of desipramine in the presence of its metabolites and imipramine, preferably for use in a fluorescence polarization immunoassay.

BACKGROUND OF THE INVENTION

Imipramine and desipramine are tricyclic antidepressant drugs which are prescribed for the treatment of chronic depression and are represented by Formula I and Formula II, respectively:

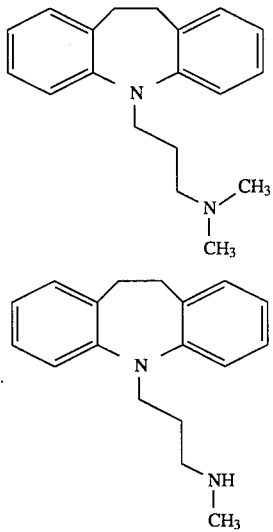

When imipramine is the primary drug for such treatment, desipramine is usually present as a naturally occurring metabolite produced by demethylation of the tertiary nitrogen of imipramine. Accordingly, desipramine is not only present when it is prescribed as the primary drug for treatment of chronic depression, but is also present when imipramine is employed as the primary drug for such treatment.

The monitoring of therapeutic drug levels of imipramine and desipramine in biological fluids such as serum, plasma, whole blood, urine, and the like, has become very useful to provide physicians with information to aid in patient management. The monitoring of such drug levels enables adjustment of patient dosage to achieve optimal therapeutic effects, and helps avoid either subtherapeutic or toxic levels, especially in the case of treatment with imipramine which results in the presence of both imipramine and desipramine. In this regard, since high levels of imipramine and desipramine have been associated with central nervous system disorders, cardiovascular toxicity, hypertension, seizures, coma and death, the concentration of imipramine and desipramine in a patient's blood must be maintained in a therapeutic range, particularly since a wide interpatient variation normally exists in human plasma for a given dose.

Accordingly, since individuals vary greatly in their response to treatment with imipramine or desipramine, it is necessary to monitor the therapy by measuring both the levels of imipramine and desipramine where imipramine is the primary drug for treatment, or measuring the level of desipramine where desipramine is the primary drug for treatment, in, for example, the serum or plasma of the patient. Concentrations below the desired therapeutic ranges are proposed to be subtherapeutic for the treatment of depression, while levels higher than the range can be associated with undesirable effects including cardiovascular complications, anticholinergic effects, and sedation, without any increase in antidepressant efficacy.

The measurement of imipramine and desipramine levels by chromatographic techniques, such as high pressure liquid chromatography [Dorey, et al., *Clin. Chem.*, 34, 2348–2351 (1988)], gas chromatography [Cooper, et al., *Psychopharmacol. Comm.*, 1, 445–454 (1975)], thin-layer chromatography [Nagy, et al., *J. Pharm. Pharmacol.*, 25, 599–603 (1973)], have been described. However, such techniques are labor intensive, requiring highly skilled personnel to perform various cumbersome steps which are time consuming and tedious.

The immunoassay determination of the levels of tricyclic antidepressant drugs, such as by radioimmunoassay (RIA) techniques [Midha, et al., *J. Analyt. Toxic.*, 2, 185–192 (1978)], by enzyme linked immunosorbent assay (ELISA) techniques [Denis, et al., *Clin. Chem. Acta*, 159, 257–267 (1986)], by fluorescence polarization immunoassay (FPIA) techniques [U.S. Pat. No. 4,420,568 and European Patent Application No. 226,730], and by enzyme immunoassay (EIA) techniques [U.S. Pat. No. 4,551,275 and U.S. Pat. No. 4,275,160], have been described. However, these techniques suffer from either a lack of specificity, i.e. determination of imipramine in the presence of desipramine and imipramine metabolites, and determination of desipramine in the presence of imipramine and desipramine metabolites, or require labor-intensive column purification to overcome the lack of antibody specificity in the presence of the analyte's metabolites. In particular, a non-specific fluorescence polarization immunoassay (FPIA) for the detection of the total amount of the four major tricyclic antidepressant drugs is commercially available and described in European Patent Application Publication No. 226,730 and U.S. Pat. No. 4,420,568 wherein the concentration determined by this assay is only an estimation of the total amount of tricyclic antidepressant in plasma or serum. Accordingly, such assay cannot be used to accurately quantify a specific individual tricyclic antidepressant drug, for example, in a patient treated with imipramine, but instead, would give the total amount of imipramine and desipramine in the patient's plasma or serum.

SUMMARY OF THE INVENTION

The present invention provides unique antibody reagents and labeled reagents for the quantification of imipramine or desipramine in a test sample. The present invention also provides synthetic procedures for preparing immunogens which are employed for the production of such antibody reagents, and for preparing such labeled reagents. According to the present invention, the labeled reagents and the antibody reagents offer an advance in the art beyond previously known procedures when used in an immunoassay for the quantification of imipramine or desipramine in a test sample. According to a preferred embodiment of the present invention, labeled reagents and antibody reagents are described for use in a fluorescence polarization immunoassay which combines the specificity of an immunoassay with the speed and convenience of homogeneous methods to provide the precise and reliable quantification of imipramine or desipramine in a test sample.

DETAILED DESCRIPTION OF THE INVENTION

According to the present invention, the specific quantification of imipramine or desipramine is accomplished by first contacting the test sample with a labeled reagent, or tracer, and an antibody reagent, either simultaneously or sequentially in either order, and then measuring the amount of the labeled reagent which either has or has not participated in a binding reaction with the antibody reagent as a function of the amount of imipramine or desipramine in the test sample.

In particular, the present invention relates to immunogens, antibodies prepared from such immunogens, and labeled reagents for use in the fluorescence polarization immunoassays for the specific quantification of imipramine and for use in the specific quantification of desipramine. It is to be understood that the specific quantification of imipramine or desipramine according to the present invention is intended to mean that, for an imipramine immunoassay, the specific quantification of imipramine is accomplished in the presence of desipramine and imipramine metabolites, and for a desipramine immunoassay, the specific quantification of desipramine is accomplished in the presence of imipramine and desipramine metabolites.

Antibodies of the present invention are produced with immunogens which are prepared with derivatives of the Formula III:

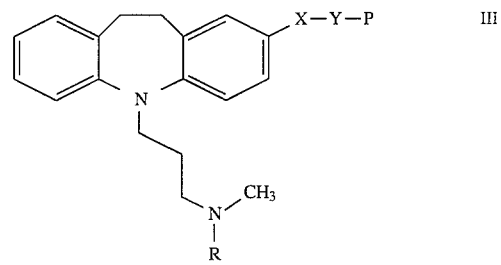

where P is an immunogenic carrier material, wherein for the quantification of imipramine, R is $CH_3$, X is two heteroatoms linked together, and Y is a linking group comprising from 1 to 6 carbon atoms, and for the quantification of desipramine, R is H, X is two heteroatoms linked together, and Y is a linking group comprising from 1 to 6 carbon atoms.

Labeled reagents of the present invention are prepared with derivatives of the Formula IV:

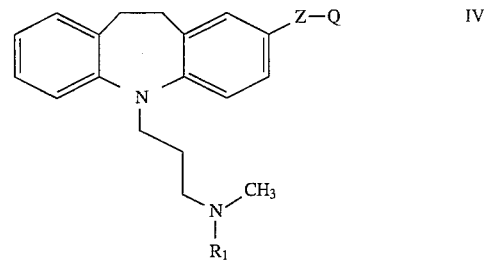

where Q is a detectable moiety, preferably a fluorescent moiety, and wherein for the quantification of imipramine, $R_1$ is $CH_3$, and Z is a linking group comprising from 1 to 4 carbon atoms and 0 to 2 heteroatoms, and for the quantification of desipramine, $R_1$ is H, and Z is a linking group comprising from 1 to 4 carbon atoms and 0 to 2 heteroatoms.

Figure 1A:
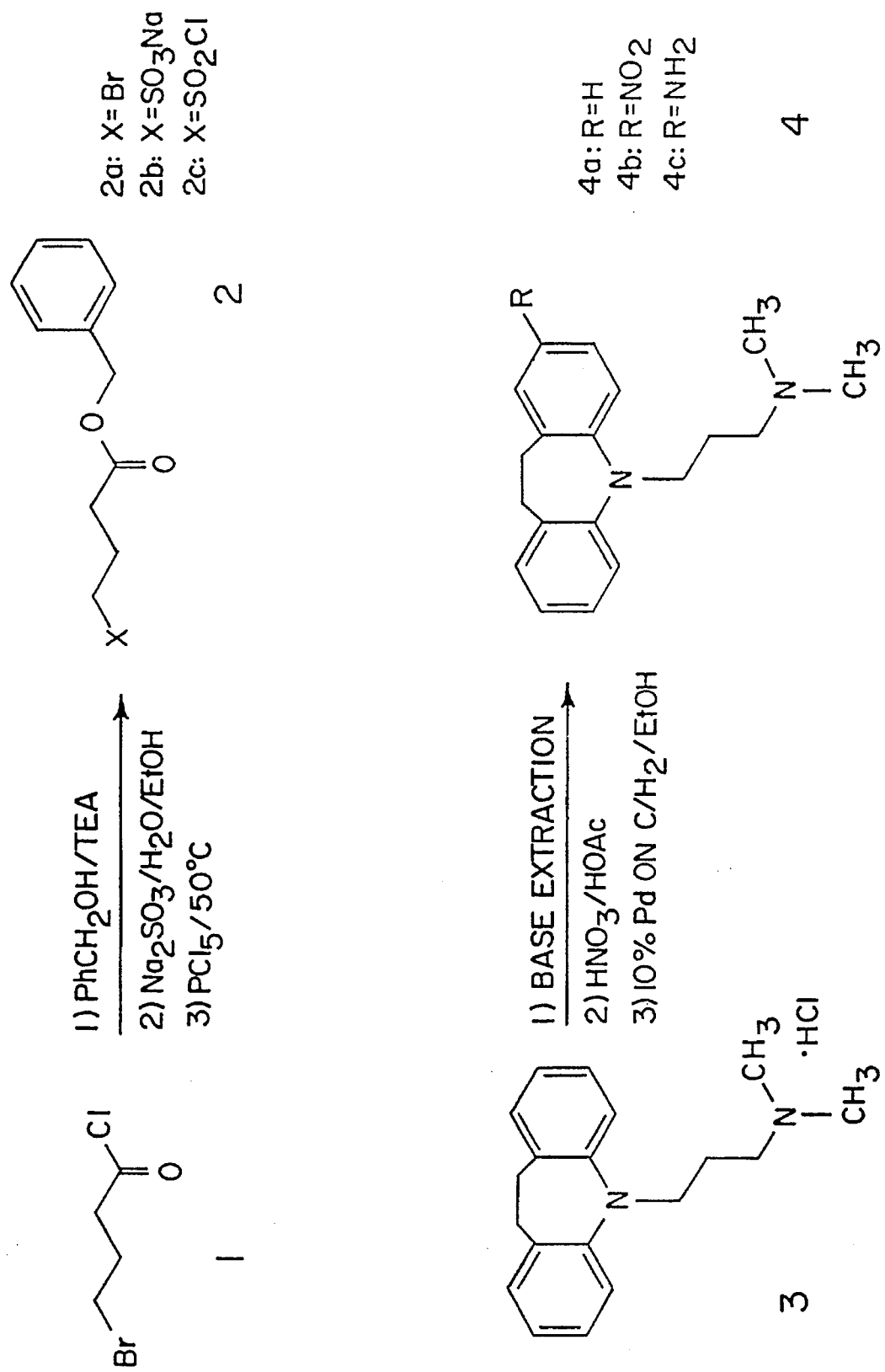
FIGS. 1A and 1B illustrate the synthetic pathway for coupling imipramine to bovine serum albumin according to the method of the present invention.
Figure 1B:
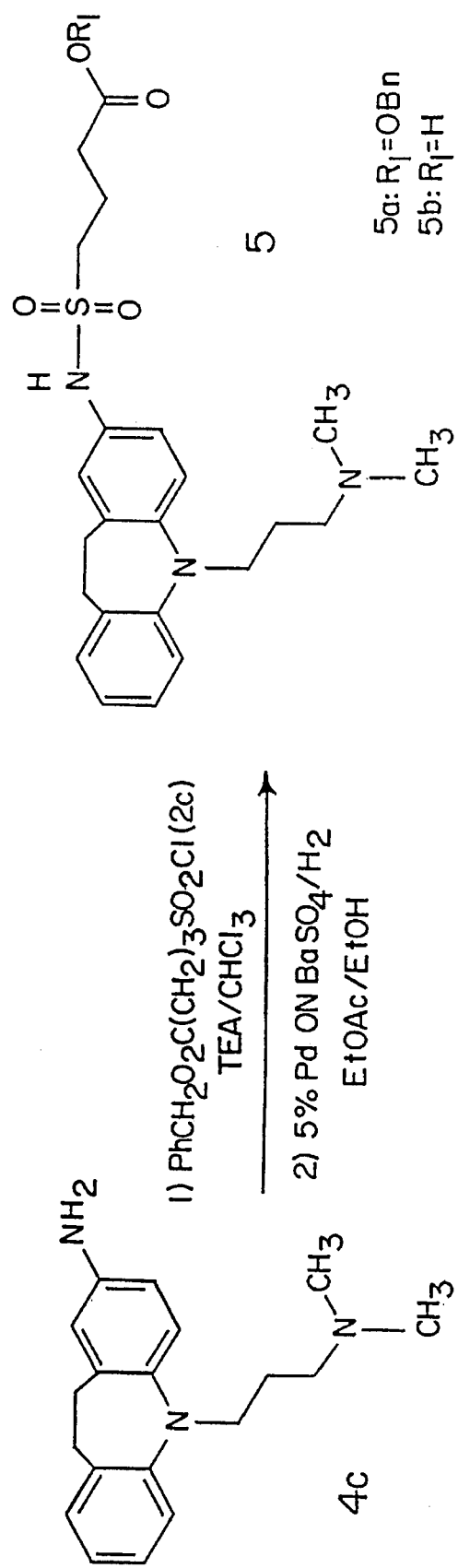
Figure 1B:
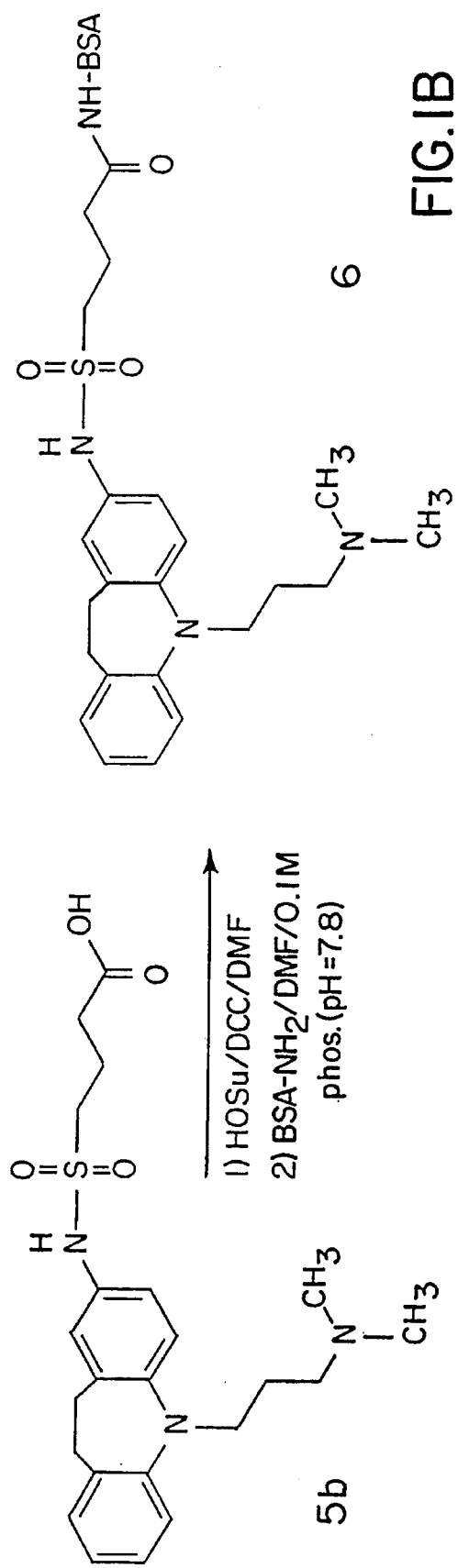
Figure 2A:
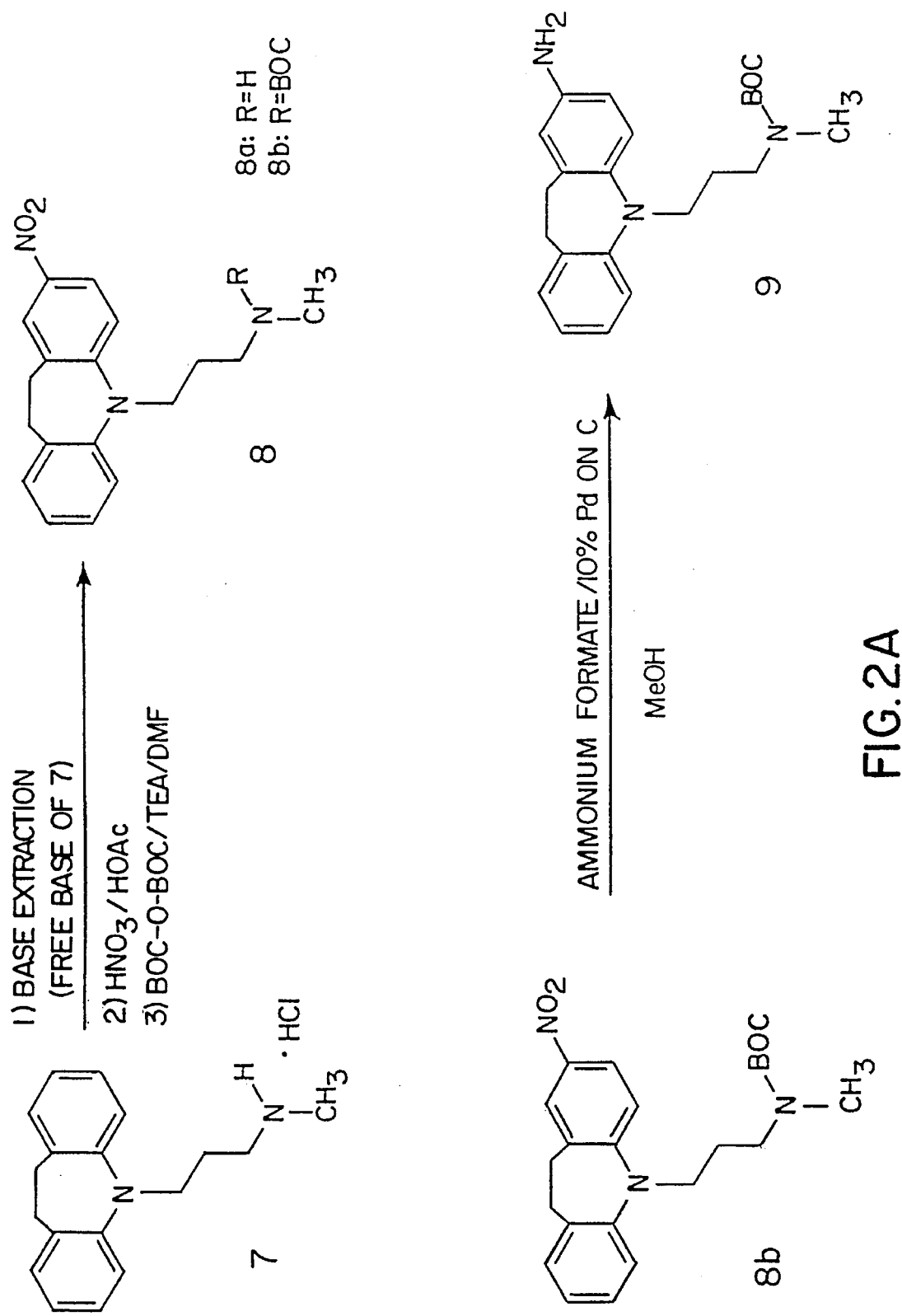
FIGS. 2A and 2B illustrate the synthetic pathway for coupling desipramine to bovine serum albumin according to the method of the present invention.
Figure 2B:
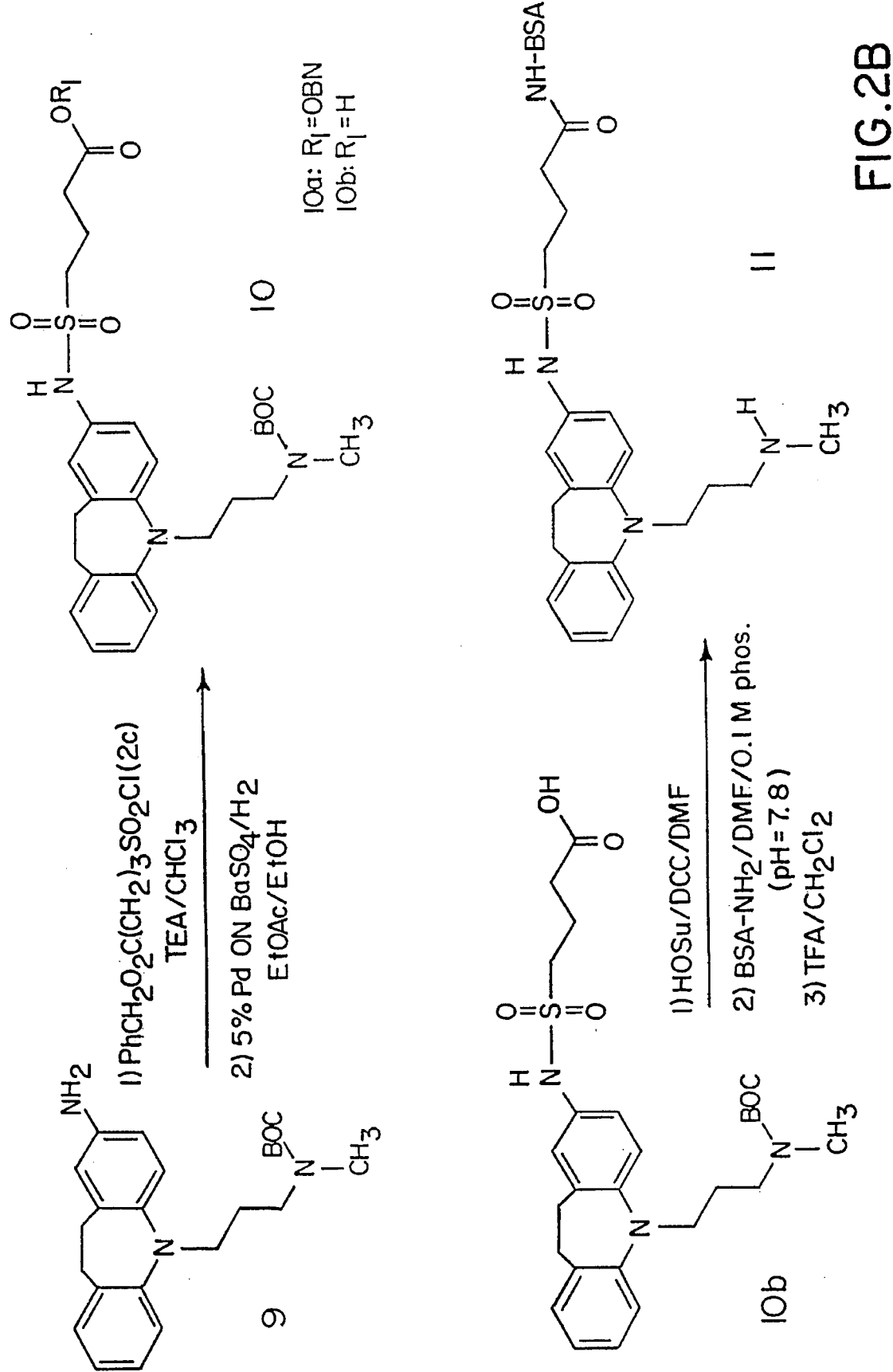
Figure 3A:
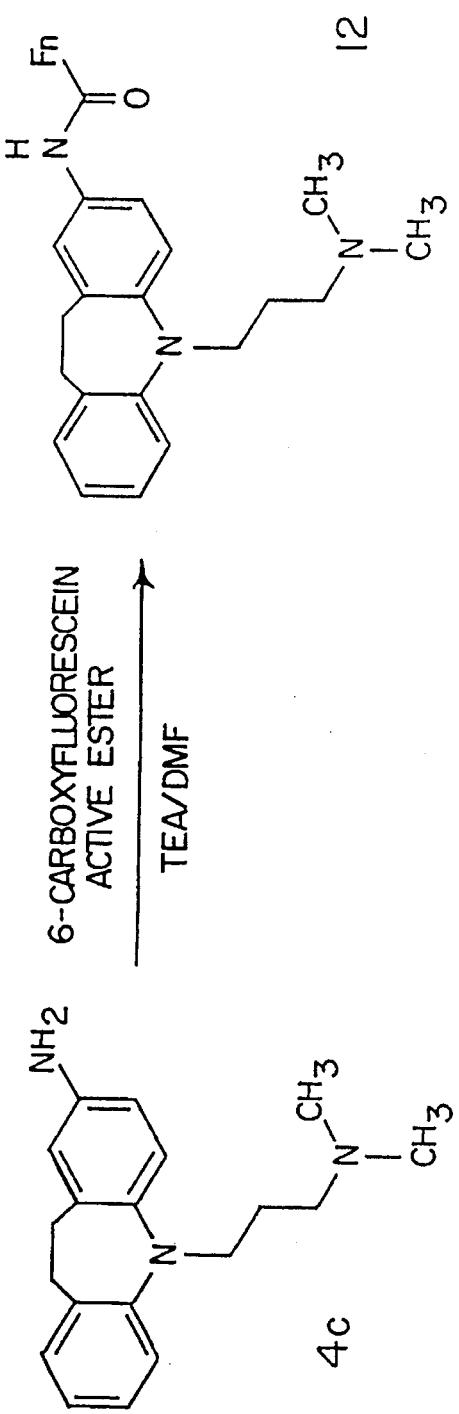
FIG. 3A Illustrates the synthetic pathway for coupling imipramine to 6-carboxyfluorescein and desipramine to 6-carboxyfluorescein according to the method of the present invention and the structures of 6-carboxyfluorescein active ester and the 6-fluoresceinyl substituents.
Figure 3A:
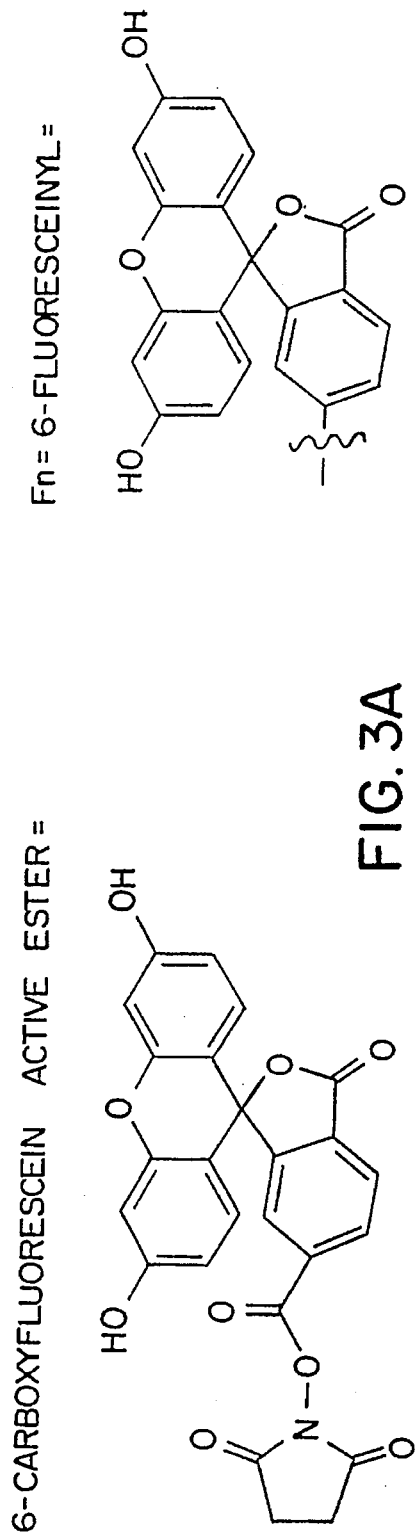
Figure 3B:
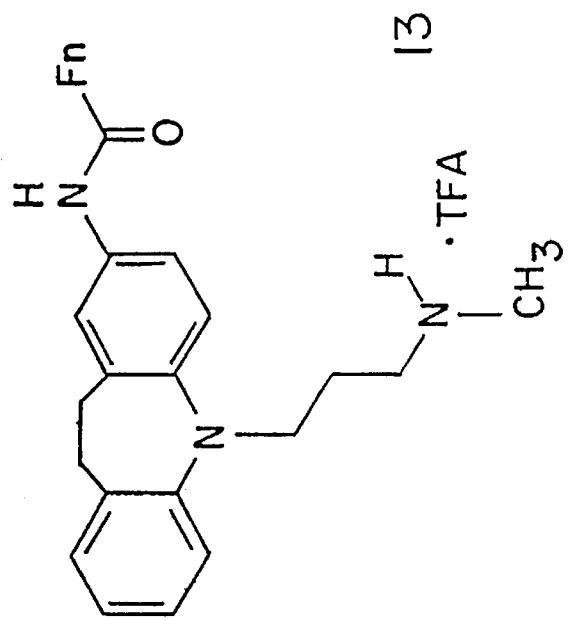
FIG. 3B illustrates the synthetic pathway for coupling desipramine to 6-carboxyfluorescein according to the method of the present invention.
Figure 3B:
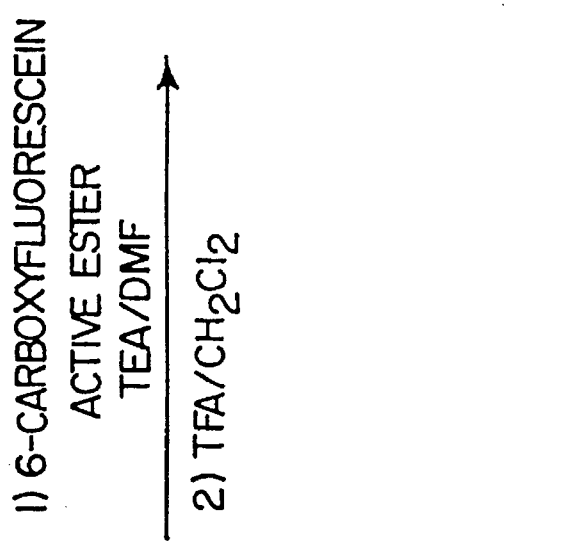
Figure 3B:
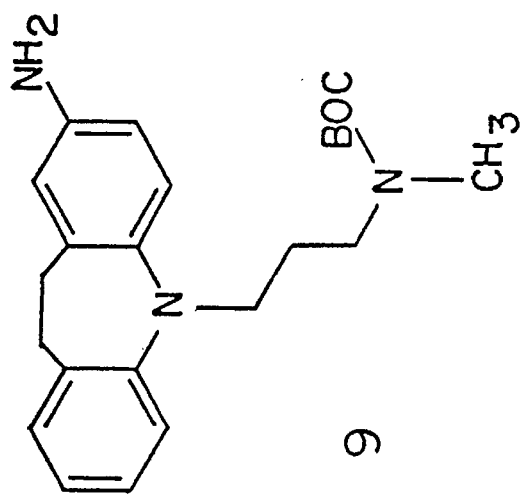

The immunogens of the present invention are prepared as described below and as shown in FIG. 1 (imipramine immunogen) and FIG. 2 (desipramine immunogen). For the preparation of an imipramine immunogen, 2-aminoimipramine, prepared by the nitration of imipramine and subsequent reduction, was reacted with carbobenzyloxypropylsulfonyl chloride to yield a unique sulfonamide. The sulfonamide was debenzylated to afford the free acid which was conjugated to bovine serum albumin through the hydroxysuccinimido active ester to give the desired imipramine immunogen. For the preparation of a desipramine immunogen, N'-BOC protected-2-aminodesipramine, prepared from 2-nitrodesipramine, was reacted with carbobenzyloxypropylsulfonyl chloride to yield a unique sulfonamide. This sulfonamide was debenzylated to afford the N'-BOC free acid which was conjugated to bovine serum albumin through the hydroxysuccinimido active ester to give the N'-BOC protected compound. After treatment with trifluoroacetic acid, the desired desipramine immunogen was obtained.

A preferred fluorescent imipramine labeled reagent for use in a specific fluorescence polarization immunoassay for imipramine was synthesized by condensing 2-aminoimipramine with the 6-carboxyfluorescein hydroxysuccinimido active ester to afford the imipramine tracer as shown in FIG. 3. A preferred fluorescent desipramine labeled reagent as described above for use in a specific fluorescence polarization immunoassay for desipramine was synthesized by condensing N'-BOC protected-2-aminodesipramine with the 6-carboxyfluorescein hydroxysuccinimido active ester to afford the N'-BOC protected tracer. After treatment with trifluoroacetic acid, the desired desipramine tracer shown in FIG. 3 was obtained.

Figure 5:
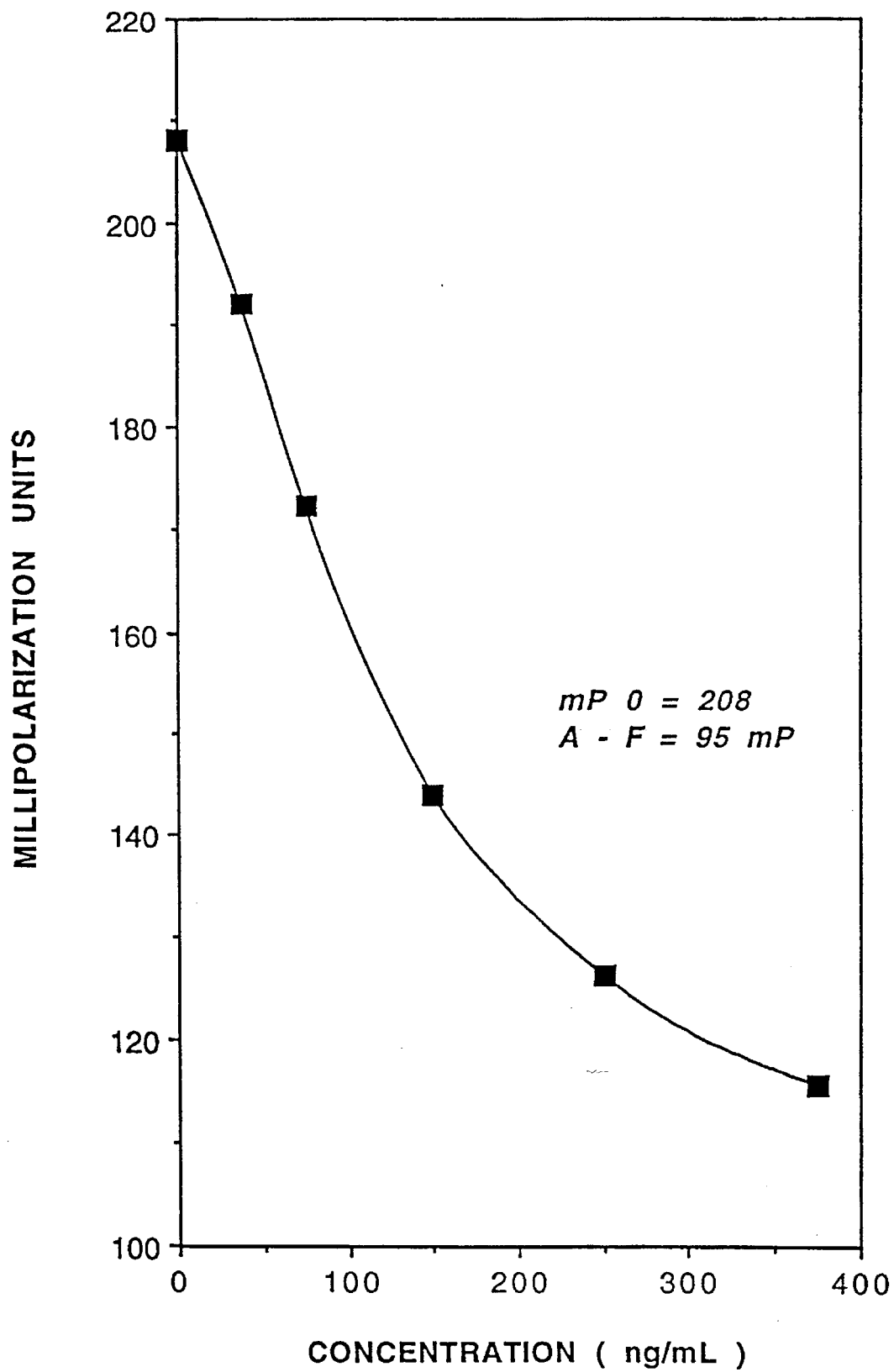
FIG. 5 is a graph which illustrates an imipramine calibration curve on the Abbott TDx® analyzer.
Figure 6:
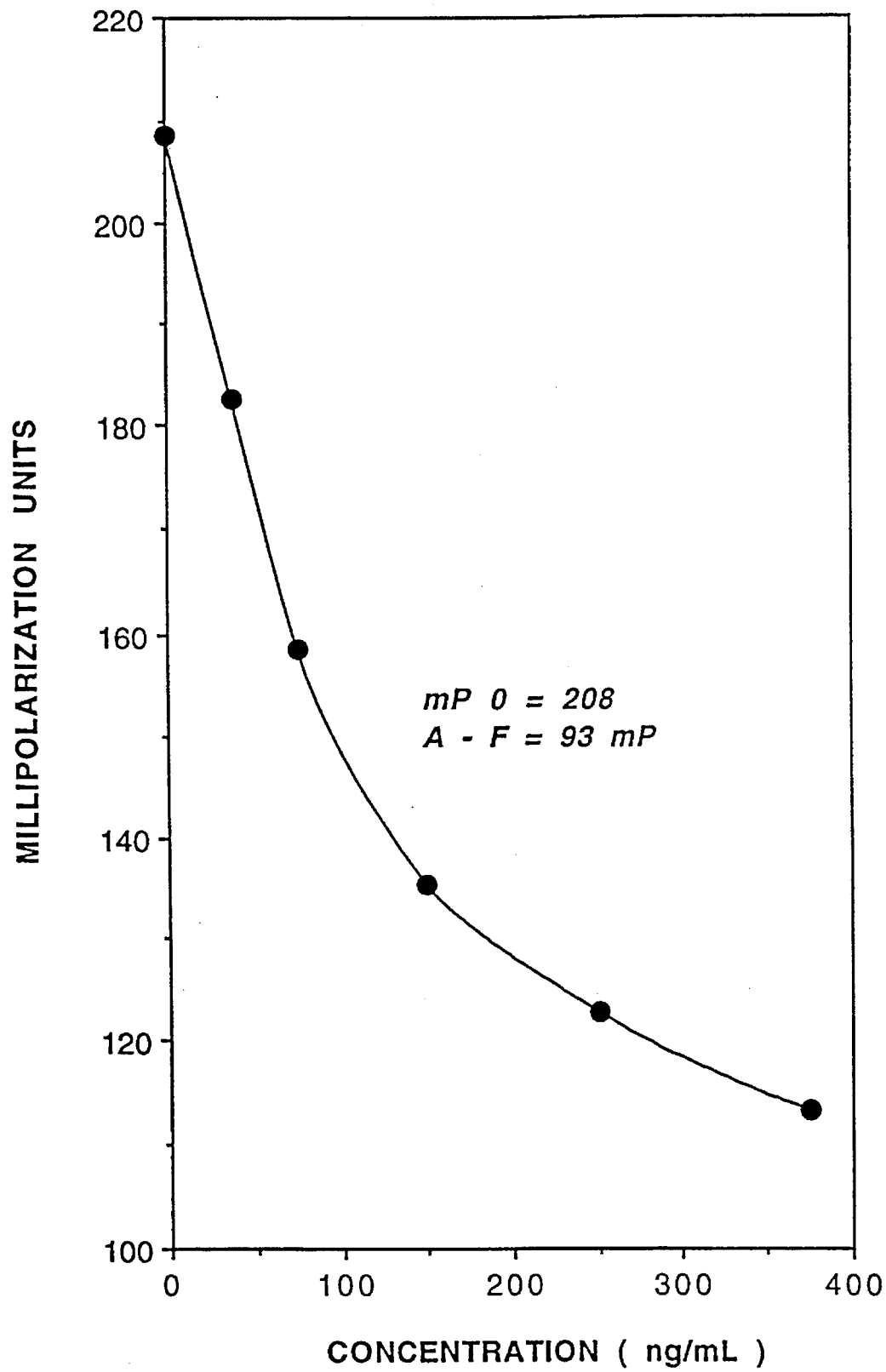
FIG. 6 is a graph which illustrates an desipramine calibration curve on the Abbott TDx® analyzer.

When following a fluorescence polarization immunoassay (FPIA) format employing the reagents according to the present invention, the concentration, or level, of either imipramine or desipramine in a test sample can be accurately quantified. To perform a FPIA for the specific quantification of imipramine or desipramine, calibration curves were generated for monitoring the therapeutic range of imipramine (FIG. 5) and desipramine (FIG. 6).

According to the present invention, it has been unexpectedly and surprisingly found that superior fluorescence polarization immunoassay assay results for the quantification of imipramine or desipramine are obtained when employing (i) an antibody reagent comprising antibodies produced from an imipramine or desipramine immunogen of Formula III where P is an immunogenic carrier as described above and (ii) a fluorescent labeled reagent of Formula IV where Q is a fluorescent moiety as described above. For the quantification of imipramine, the antibody reagent comprises antibodies which are capable of binding to or recognizing imipramine wherein the antibodies are preferably produced with an immunogen prepared from the imipramine derivative of Formula III where P is bovine serum albumin, X is —NH—$SO_2$—, and Y is —$(CH_2)_3$—CO—, and the labeled reagent is preferably prepared from the imipramine derivative of Formula IV where Q is a fluorescent moiety, Z is —NH—CO—, and $R_1$ is $CH_3$. Similarly, for the quantification of desipramine, the antibody reagent comprises antibodies which are capable of binding to or recognizing desipramine wherein the antibodies are preferably produced with an immunogen prepared from the desipramine derivative of Formula III where P is bovine serum albumin, X is —NH—$SO_2$—, $R_1$ is H, and Y is —$(CH_2)_3$—CO, and the labeled reagent is preferably prepared from the desipramine derivative of Formula IV where Q is a fluorescent moiety, Z is —NH—CO—, and $R_1$ is H.

Figure 7:
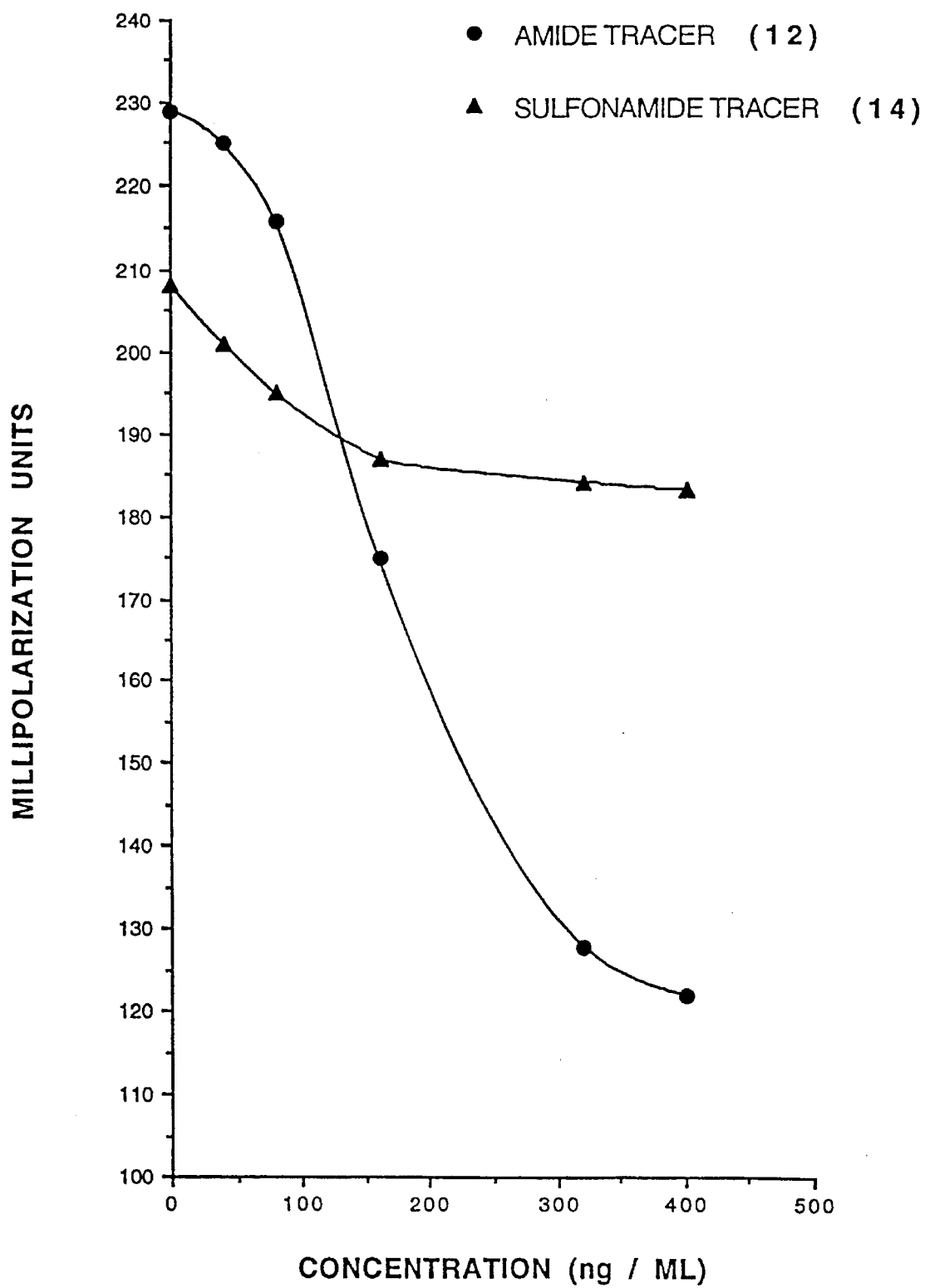
FIG. 7 is a graph which illustrates the effects of structural modification of a fluorescent tracer on a specific imipramine assay.
Figure 9:
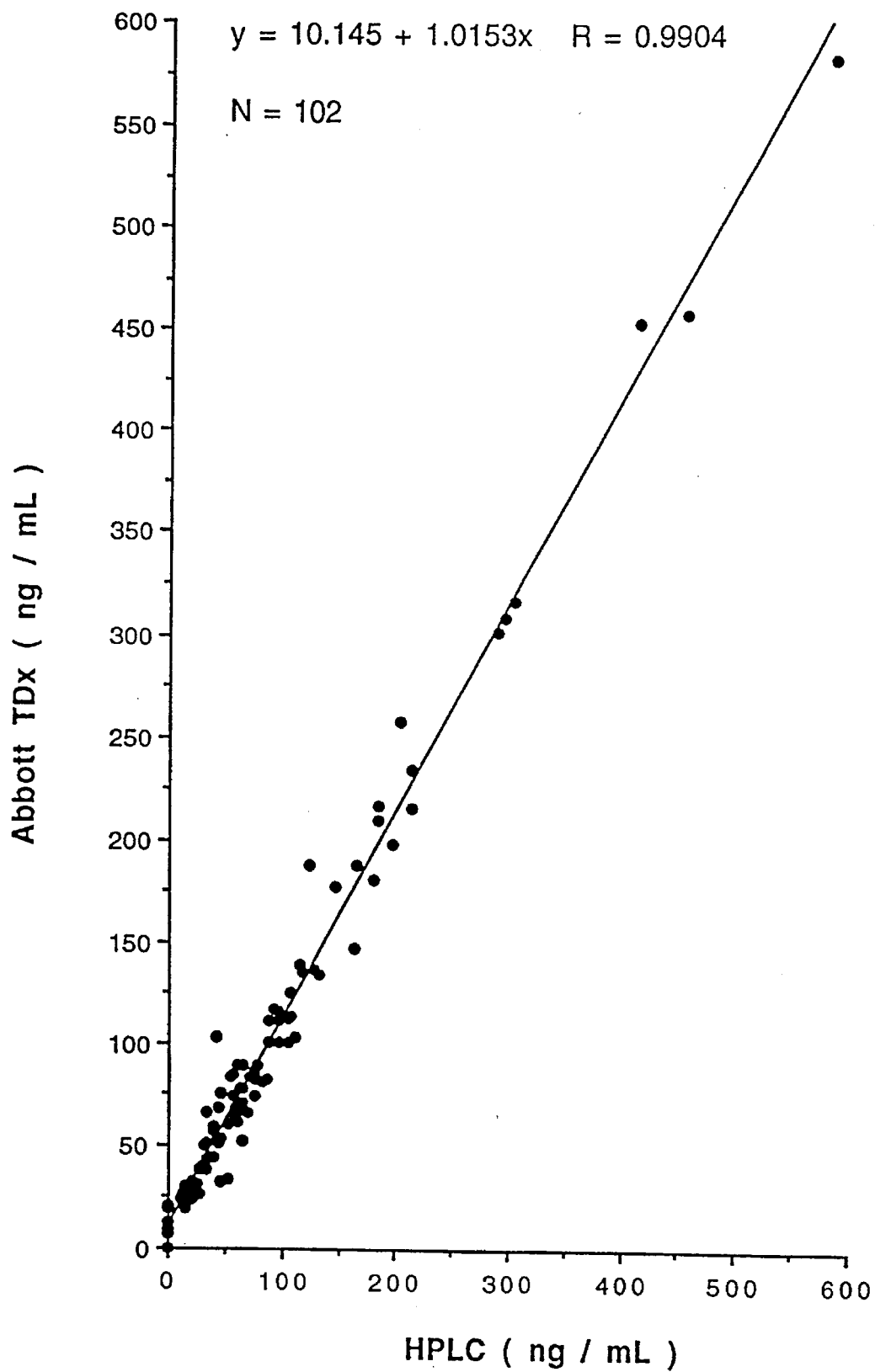
FIG. 9 is a graph which illustrates the accuracy of the method of fluorescence polarization immunoassay for the specific quantification of imipramine of the present invention compared to high performance liquid chromatography.

In particular, it was unexpectedly and surprisingly found that for the specific quantification of imipramine, the combination of the novel immunogen of Formula III, wherein R is $CH_3$ and which contains a sulfonamide group linked to the aromatic ring [X=(—NH—$SO_2$—)], and a novel fluorescent tracer of Formula IV, wherein $R_1$ is $CH_3$ and which contains an amide group linked to the aromatic ring [Z=(—NH—CO—)], was critical for the specific quantification of imipramine as intended by the present invention. This advantageous combination of unique reagents offers an advance in the art for the specific quantification of imipramine. For the specific quantification of desipramine, the unique combination of reagents comprising the novel immunogen of Formula III, wherein R is H and which contains a sulfonamide group linked to the aromatic ring [X=(—NH—$SO_2$—)], and a novel fluorescent tracer of Formula IV, wherein $R_1$ is H and which contains an amide group linked to the aromatic ring [Z=(—NH—CO—)], was critical for the specific quantification of desipramine as intended by the present invention. This advantageous combination of unique reagents offers an advance in the art for the specific quantification of desipramine. The performance of the above combinations is illustrated in FIGS. 7 (imipramine) and 8 (desipramine) while correlation with high-performance liquid chromatography (HPLC) is illustrated in FIGS. 9 (imipramine) and 10 (desipramine).

When performing a fluorescence polarization immunoassay for the specific quantification of imipramine or desipramine as described herein, the detectable moiety component of the tracer is a fluorescent moiety such as fluoresceins, aminofluoresceins, carboxyfluoresceins, and the like, preferably aminomethylfluorescein, aminofluorescein, 5-fluoresceinyl, 6-fluoresceinyl, 6-carboxyfluorescein, 5-carboxyfluorescein, thiourea-aminofluorescein, and methoxytriazinolyl-aminofluorescein, and the like fluorescent derivatives. The amount of tracer bound to the antibody varies inversely to the amount of imipramine or desipramine present in the test sample. Accordingly, the relative, and therefore characteristic, binding affinities of imipramine or desipramine and the tracer to the antibody binding site, are important parameters of the assay system. Generally, fluorescent polarization techniques are based on the principle that a fluorescent tracer, when excited by plane polarized light of a characteristic wavelength, will emit light at another characteristic wavelength (i.e., fluorescence) that retains a degree of the polarization relative to the incident stimulating light that is inversely related to the rate of rotation of the tracer in a given medium. As a consequence of this property, a tracer substance with constrained rotation, such as in a viscous solution phase or when bound to another solution component with a relatively lower rate of rotation, will retain a relatively greater degree of polarization of emitted light than if in free solution. Therefore, within the time frame in which the ligand and tracer compete for binding to the antibody, the tracer and ligand binding rates should yield an appropriate proportion of free and bound tracer with the preservation of important performance parameters such as selectivity, sensitivity, and precision.

When performing a fluorescent polarization immunoassay for the specific quantification of imipramine or desipramine according to the present invention, a test sample suspected of containing imipramine or desipramine is contacted with antiserum prepared with immunogens according to the present invention in the presence of an appropriately selected fluorescein derivative thereof which is capable of producing a detectable fluorescence polarization response to the presence of antiserum prepared with immunogens according to the present invention. Plane polarized light is then passed through the solution to obtain a fluorescent polarization response and the response is detected as a measure of amount of imipramine or desipramine present in the test sample.

The imipramine and desipramine derivatives of the present invention are employed to prepare immunogens by coupling them to conventional carrier materials, and subsequently used to obtain antibodies. The imipramine and desipramine derivatives are also used to prepare labeled reagents which serve as the detection reagents in immunoassays for quantifying imipramine or desipramine in a test sample. The imipramine and desipramine derivatives of the present invention can be coupled to immunogenic carrier materials by various conventional techniques known in the art where P is an immunogenic carrier material in Formula III. As would be understood by one skilled in the art, the immunogenic carrier material can be selected from any of those conventionally known and, in most instances, will be a protein or polypeptide, although other materials such as carbohydrates, polysaccharides, lipopolysaccharides, poly(amino) acids, nucleic acids, and the like, of sufficient size and immunogenicity can also be employed. Preferably, the immunogenic carrier material is a protein such as bovine serum albumin, keyhole limpet hemocyanin, thyroglobulin, and the like. The immunogens according to the present invention are used to prepare antibodies, both polyclonal and monoclonal, according to methods known in the art for use in an immunoassay system according to the present invention. Generally, a host animal, such as a rabbit, goat, mouse, guinea pig, or horse is injected at one or more of a variety of sites with the immunogen, normally in mixture with an adjuvant. Further injections are made at the same site or different sites at regular or irregular intervals thereafter with bleedings being taken to assess antibody titer until it is determined that optimal titer has been reached. The antibodies are obtained by either bleeding the host animal to yield a volume of antiserum, or by somatic cell hybridization techniques or other techniques known in the art to obtain monoclonal antibodies, and can be stored, for example, at $-20°$ C.

In addition to fluorescence polarization immunoassays, various other immunoassay formats can be followed for the quantification of imipramine or desipramine according to the present invention. Such immunoassay system formats include, but are not intended to be limited to, competitive, sandwich and immunometric techniques. Generally, such immunoassay systems depend upon the ability of an immunoglobulin, i.e., a whole antibody or fragment thereof, to bind to a specific analyte from a test sample wherein a labeled reagent comprising an antibody of the present invention, or fragment thereof, and a label or detectable moiety is employed to determine the extent of binding. Such detectable labels include, but are not intended to be limited to, enzymes, radiolabels, biotin, toxins, drugs, haptens, DNA, RNA, liposomes, chromophores, chemiluminescers, colored particles and colored microparticles, fluorescent compounds and derivatives such as aminomethylfluorescein, 5-fluoresceinyl, 6-fluoresceinyl, 5-carboxyfluorescein, 6-carboxyfluorescein, amino-fluorescein, thioureafluorescein, and methoxytriazinolyl-aminofluorescein, and the like fluorescent derivatives. As described herein, the test sample can be a naturally occurring or artificially formed liquid, or an extract thereof, and includes, but is not intended to be limited to biological test samples such as whole blood, serum, plasma, urine, feces, saliva, cerebrospinal fluid, brain tissue, and the like. In addition, the test sample can be an extract of a test sample, or any derivative thereof.

Typically, the extent of binding in such immunoassay system formats is determined by the amount of the detectable moiety present in the labeled reagent which either has or has not participated in a binding reaction with the analyte, wherein the amount of the detectable moiety detected and measured can be correlated to the amount of analyte present in the test sample. For example, in a competitive immunoassay system, a substance being measured, often referred to as a ligand, competes with a substance of close structural similarity coupled to a detectable moiety, often referred to as a tracer, for a limited number of binding sites on antibodies specific to the portion or portions of the ligand and tracer with structural similarity, shared with an immunogen employed to produce such antibodies. It is to be understood that since desipramine will be present in a test sample as the metabolite of imipramine where the drug for treatment is imipramine, the amount of imipramine and desipramine are determined in separate immunoassay systems employing the imipramine and desipramine derivatives, respectively, of the present invention.

A test kit according to the present invention comprises all of the essential reagents required to perform a desired specific fluorescence polarization immunoassay according to the present invention for the quantification of imipramine in a test sample, or for the quantification of desipramine in a test sample, as described herein. The test kit is presented in a commercially packaged form as a combination of one or more containers holding the necessary reagents, as a composition or admixture where the compatibility of the reagents will allow. Particularly preferred is a test kit for the fluorescence polarization immunoassay quantification of imipramine in a test sample or for the fluorescence polarization immunoassay quantification of desipramine in a test sample, comprising fluorescent tracer compounds of the present invention and antibodies of the present invention produced with the immunogens as described above for the respective quantification of either imipramine or desipramine. It is to be understood that the test kit can, of course, include other materials as are known in the art and which may be desirable from a commercial user standpoint, such as buffers, diluents, standards, and the like.

The present invention will now be illustrated, but is not intended to be limited by, the following examples. Boldfaced numerals contained in parenthesis refer to the structural formulae as used in the Figures:

EXAMPLE 1

SYNTHESIS OF IMIPRAMINE IMMUNOGEN
(6)

(a) Solvent abbreviations: $CHCl_3$=chloroform, MeOH=methanol, DMF=dimethylformamide, $CH_2Cl_2$=methylene chloride, $Et_2O$=diethyl ether, EtOAc=ethyl acetate, Hex=hexane, THF=tetrahydrofuran, HOAc=acetic acid. All solvent mixtures are volume/volume.

(b) Benzyl alcohol (28 mL, 270 mmol) and triethylamine (3.8 mL, 27 mmol) were combined and stirred over an ice bath, under nitrogen ($N_2$). 4-Bromobutyryl chloride (1) (3.1 mL, 27 mmol) was added in a dropwise fashion, then the reaction was stirred an additional 30 minutes. The completed reaction was poured into 250 mL $H_2O$ and extracted with $Et_2O$ (3×200 mL). The ether extracts were combined, dried over $MgSO_4$, and solvent removed in vacuo. Resulting crude product was purified by column chromatography, eluting with EtOAc/Hex (10/90) to afford 2.55 g (37%) of the desired benzyl 4-bromobutyrate (2a). $^1$H NMR (200 MHz, $CDCl_3$) d 7.4 (s, 5H), 5.2 (s, 2H), 3.4 (t, 2H), 2.6 (t, 2H), 2.2 (p, 2H); mass spec (DCl, $NH_3$) $(M+NH_4)^+$275.

Benzyl 4-bromobutyrate (2a) (2.53 g, 9.85 mmol) was dissolved in 1.9 mL EtOH and added dropwise to a stirred 0° C. solution of sodium sulfite (1.24 g, 9.85 mmol) in 4.8 mL $H_2O$, then reaction refluxed for 4 hours. Solvent was removed in vacuo to give a white solid which was recrystallized from EtOH to afford 1.17 g (42%) of the desired salt (2b). $^1$H NMR (200 MHz, DMSO-$d_6$) d 7.4 (s, 5H), 5.2 (s, 2H), 2.6–2.4 (m, 4H), 1.9 (p, 2H); mass spec (FAB) $(M+H)^+$ 257.

The sodium salt (2b) (548 mg, 1.96 mmol) was combined with phosphorus pentachloride (816 mg, 3.92 mmol), the resulting mixture was heated and stirred at 50° C. for 30 minutes. The reaction was then diluted with 40 mL ice water and extracted with $CHCl_3$ (3×40 mL). The $CHCl_3$ extracts were combined, washed with 40 mL brine (saturated aqueous NaCl), dried over $Na_2SO_4$, and solvent removed in vacuo to yield 440 mg (81%) of the desired product (2c). $^1H$ NMR (200 MHz, $CDCl_3$) d 7.5–7.1 (m, 5H), 5.2 (s, 2H), 3.8 (t, 2H), 2.6 (t, 2H), 2.3 (p, 2H).

Imipramine hydrochloride (3) (2.21 g, 6.97 mmol) was dissolved in 35 mL $H_2O$, made basic with 6M NaOH, and extracted with $CHCl_3$ (3×35 mL). The $CHCl_3$ extracts were combined, washed with 35 mL brine, dried over $Na_2SO_4$, and solvent removed in vacuo to afford 1.95 g of the desired imipramine free base (4a). $^1H$ NMR (200 MHz, $CDCl_3$) d.7.2–7.1 (m, 6H), 7.0–6.8 (m, 2H), 3.8 (t, 2H), 3.2 (s, 4H), 2.3 (t, 2H), 2.1 (s, 6H), 1.7 (p, 2H).

Imipramine (4a) (1.925 g, 6.87 mmol) was dissolved in 32 mL acetic acid and cooled to 18° C. Concentrated nitric acid (0.79 mL, 13 mmol) in 1.1 mL acetic acid was added dropwise, with stirring, keeping reaction at 17°–18° C., then reaction stirred at that temperature for an additional 20 minutes. The reaction was then poured into 130 mL of 0.15M HCl and washed with $Et_2O$ (2×85 mL), the pH was adjusted to 13 with 10N NaOH and extracted with $CHCl_3$ (4×100 mL). The $CHCl_3$ extracts were combined, washed with 85 mL brine, dried over $Na_2SO_4$, and solvent removed in vacuo. The residue was purified by column chromatography, eluting with $THF/Hex/NH_4OH$ (70/30/0.4) to yield 1.145 g (51%) of the desired 2-nitroimipramine (4b) as a red oil. $^1H$ NMR (200 MHz, $CDCl_3$) d 8.0–7.9 (m, 2H), 7.3–7.0 (m, 5H), 3.9 (t, 2H), 3.2 (s, 4H), 2.3 (t, 2H), 2.1 (s, 6H), 1.7 (p, 2H); mass spec (FAB) $(M+H)^+326$.

2-Nitroimipramine (4b) (552 mg, 1.70 mmol) was dissolved in 20 mL absolute EtOH, 55 mg of 10% palladium on carbon added, and reaction stirred under $H_2$ (balloon pressure) for 3.5 hours. The reaction was vacuum filtered through Celite and filtrate solvents were removed in vacuo to afford 499 mg (99%) of the desired 2-aminoimipramine (4c) as a pale yellow oil. $^1H$ NMR (200 MHz, $CDCl_3$) d 7.2–7.0 (m, 3H), 6.9–6.8 (m, 2H), 6.5–6.4 (m, 2H), 3.7 (t, 2H), 3.2–3.0 (m, 4H), 2.3 (t, 2H), 2.1 (s, 6H), 1.7 (p, 2H); mass spec (FAB) $(M+H)^+296$.

A solution of the ester (2c) (431 mg, 1.56 mmol)/2.7 mL $CH_2Cl_2$ was added in a dropwise fashion to a stirred, 0° C. solution of 2-aminoimipramine (4c) (420 mg, 1.42 mmol)and triethylamine (0.40 mL, 2.8 mmol) dissolved in 2.7 mL $CH2Cl_2$ under $N_2$. The reaction was stirred an additional 20 minutes at 0° C., then solvents removed in vacuo and residue purified by column chromatography, eluting with $CH_2Cl_2/MeOH$ (90/10), to yield 324 mg (43%) of the desired product (5a) as a yellow solid. $^1H$ NMR (200 MHz, $CDCl_3$) d 7.5–6.8 (m, 12H), 5.1 (s, 2H), 3.8 (t, 2H), 3.1 (s, 4H), 3.1 (t, 2H), 2.8 (t, 2H), 2.5 (s, 6H), 2.5 (t, 2H), 2.2 (p, 2H), 2.0 (p, 2H); mass spec (DCl, $NH_3$) $(M+H)^+536$.

The benzyl ester (5a) (299 mg, 0.56 mmol) was dissolved in 8 mL of EtOAc/abs. EtOH (70/30), 100 mg of 5% palladium on barium sulfate added, and reaction stirred under $H_2$ (balloon pressure) for 3 hours. The reaction was filtered, filtrate solvent removed in vacuo, residue recombined with 3 mL of reaction solvent and 100 mg catalyst, and stirring under $H_2$ resumed. After 17 hours the reaction was again filtered, rotoevaporated, and started again with fresh solvent and catalyst. After 24 hours stirring under $H_2$ (balloon), the reaction was filtered and filtrate solvent removed in vacuo to afford 229 mg (92%) of the desired acid (5b) as a white solid. $^1H$ NMR (200 MHz, $CD_3OD$) d 7.4–6.9 (m, 7H), 3.8 (t, 2H), 3.2–3.0 (m, 8H), 2.7 (s, 6H), 2.3 (t, 2H), 2.1–1.9 (m, 4H); mass spec (FAB) $(M+H)^+446$.

The acid (5b) (74 mg, 0.17 mmol) was dissolved in 0.77 mL DMF, N-hydroxysuccinimide (HOSu, 23 mg, 0.20 mmol) added, 1,3-dicyclohexylcar-bodiimide (DCC, 41 mg, 0.20 mmol) added, and reaction stirred for 17 hours, under $N_2$. The reaction was filtered and filtrate added to a solution of bovine serum albumin (BSA, 289 mg, 0.0043 mmol) dissolved in 4.8 mL of 0.1M sodium phosphate (pH=7.8) and 1.3 mL DMF. After stirring overnight, the reaction was dialyzed against 2 L of 0.1M sodium phosphate (pH=7.8) for 4 hours, then against $H_2O$ (7×2 L). After lyophilization 287 mg of the desired immunogen (6) was obtained as a fluffy white solid.

EXAMPLE 2

SYNTHESIS OF DESIPRAMINE IMMUNOGEN
(11)

Desipramine hydrochloride (7) (10.00 g, 33.0 mmol) was dissolved in 200 mL $H_2O$, pH adjusted to 13 with 6M NaOH, and extracted with $CHCl_3$ (3×200 mL). The $CHCl_3$ extracts were combined, washed with 200 mL brine, dried over $Na_2SO_4$, and solvent removed in vacuo to afford 9.0 g of the free base as a clear oil. $^1H$ NMR (200 MHz, $CDCl_3$) d 7.2–7.0 (m, 6H), 7.0–6.8 (m, 2H), 3.8 (t, 2H), 3.2 (s, 4H), 2.6 (t, 2H), 2.3 (s, 3H), 1.7 (p, 2H); mass spec (DCl, $NH_3$) $(M+H)^+267$.

Concentrated nitric acid (4.2 mL, 67 mmol) was dissolved in 5.6 mL acetic acid and added dropwise to a stirred, 15° C. solution of desipramine (8.97 g, 33.7 mmol) in 165 mL acetic acid, then reaction stirred 20 minutes at 15° C., then poured into 400 mL $H_2O$, treated with 9.4 mL conc. HCl, and washed with $Et_2O$ (2×250 mL). Aqueous pH was adjusted to 12 with conc. NaOH and extracted with $CHCl_3$ (3×400 mL). The $CHCl_3$ extracts were combined, dried over $Na_2SO_4$, and solvent removed in vacuo. The crude product was purified by column chromatography, eluting with $CH_2Cl_2/MeOH/NH_4OH$ (90/10/0.5), then $CH_2Cl_2/MeOH/NH_4OH$ (80/20/0.5), to afford 1.68 g (16%) of the desired 2-nitrodesipramine (8a). $^1H$ NMR (200 MHz, $CDCl_3$) d 8.1–7.9 (m, 2H), 7.3–7.0 (m, 5H), 3.9 (t, 2H), 3.2 (s, 4H), 2.6 (t, 2H), 2.3 (s, 3H), 1.8 (p, 2H); mass spec (DCl, $NH_3$) $(M+H)^+312$.

2-Nitrodesipramine (8a) (1.67 g, 5.36 mmol) was dissolved in 12 mL DMF, 1.29 g (5.90 mmol) of di-tert-butyl dicarbonate(BOC-O-BOC) added, 0.90 mL (6.4 mmol) of triethylamine added, and reaction stirred 16 hours under $N_2$, then was poured into 60 mL $H_2O$ and extracted with $Et_2O$ (3×60 mL). The ether extracts were combined, dried over $MgSO_4$, and solvent removed in vacuo. The resulting oil was purified by column chromatography, eluting with EtOAc/ Hex (20/80) to afford 1.82 g (82%) of the desired protected amine (8b). $^1H$ NMR (200 MHz, $CDCl_3$) d 8.1–7.9 (m, 2H), 7.3–7.0 (m, 5H), 3.8 (t, 2H), 3.2 (t, 2H), 3.2 (s, 4H), 2.7 (s, 3H), 1.8 (p, 2H), 1.4 (s, 9H); mass spec (DCl, $NH_3$) $(M+H)^+412$.

The nitro compound (8b) (960 mg, 2.33 mmol) was dissolved in 18 mL MeOH, 124 mg of 10% palladium on carbon was added, followed by 677 mg (10.7 mmol) of ammonium formate and reaction stirred for 45 minutes. The reaction was filtered, filtrate poured into 50 mL $H_2O$, and extracted with $CHCl_3$ (2×50 mL). The $CHCl_3$ extracts were combined, washed with 50 mL brine, dried over $Na_2SO_4$, and solvent removed in vacuo to yield 885 mg (99%) of the desired desipramine derivative (9). $^1$H NMR (200 MHz, $CDCl_3$) d 7.2–6.9 (m, 3H), 6.9–6.8 (m, 2H), 6.5–6.4 (m, 2H), 3.7 (t, 2H), 3.4 (s, 2H), 3.2 (t, 2H), 3.1 (s, 4H), 2.7 (s, 3H), 1.8 (p, 2H), 1.4 (s, 9H); mass spec (DCI, $NH_3$) (M+H)+382.

The ester (2c) (442 mg, 1.60 mmol) was dissolved in 2.9 mL $CHCl_3$ and added in a dropwise fashion, under $N_2$, to a stirred, 0° C. solution of the desipramine derivative (9) (453 mg, 1.19 mmol) and triethylamine (0.33 mL, 2.4 mmol) in 2.4 mL $CHCl_3$. The reaction was stirred an additional 1.5 hours at 0° C., then poured into 25 mL $H_2O$ and extracted with $CHCl_3$ (3×25 mL). The $CHCl_3$ extracts were combined, washed with 25 mL brine, dried over $Na_2SO_4$, and solvent removed in vacuo. The residue was purified by column chromatography, eluting with EtOAc/Hex (30/70), to yield 126 mg (17%) of the desired butyrate (10a). $^1$H NMR (200 MHz, $CDCl_3$) d 7.5–6.9 (m, 12H), 5.1 (s, 2H), 3.7 (t, 2H), 3.3 (t, 2H), 3.2 (s, 4H), 3.1 (t, 2H), 2.7 (s, 3H), 2.5 (t, 2H), 2.2 (p, 2H), 1.8 (p, 2H), 1.4 (s, 9H); mass spec (DCl, $NH_3$) $(M+H)^+622$.

The benzyl ester (10a) (120 mg, 0.193 mmol) was dissolved in 1.1 mL of EtOAc/abs. EtOH (70/30), 30 mg of 5% palladium on barium sulfate added, and reaction stirred under $H_2$ (balloon pressure) for 2.5 hours. The reaction was filtered, 40 mg fresh catalyst added to the filtrate, and stirring under $H_2$ resumed. After 17 hours the reaction was filtered and filtrate solvent removed in vacuo to afford 94 mg (91%) of the desired acid (10b). $^1$H NMR (200 MHz, $CDCl_3$) d 7.3–6.8 (m, 7H), 3.7 (t, 2H), 3.3 (t, 2H), 3.2 (s, 4H), 3.1 (t, 2H), 2.7 (s, 3H), 2.5 (t, 2H), 2.2 (m, 2H), 1.8 (p, 2H), 1.4 (s, 9H); mass spec (FAB) $(M+H)^+532$.

The acid (10b) (76 mg, 0.14 mmol) was dissolved in 0.67 mL DMF, 18 mg (0.16 mmol) of N-hydroxysuccinimide was added, 32 mg (0.16 mmol) of 1,3-dicyclohexylcarbodiimide was added, and solution stirred under $N_2$ for 24 hours. The reaction was filtered and filtrate added to a stirred solution of 243 mg (0.0036 mmol) of bovine serum albumin dissolved in 4.1 mL of 0.1M sodium phosphate (pH=7.8) and 1.1 mL DMF. After overnight stirring the reaction was dialyzed against 2 L of 0.1M sodium phosphate (pH=7.8) for 4 hours, then against $H_2O$ (7×2 L). After lyophilization, 277 mg of the desired N-BOC immunogen was obtained.

To 265 mg of the N-BOC immunogen was added 10 mL $CH_2Cl_2$, followed by 10 mL trifluoroacetic acid. After stirring 5 minutes solvent was removed in vacuo and residue redissolved in 60 mL of 0.1M sodium phosphate (pH=7.8). The resulting cloudy solution was dialyzed against 2 L of 0.1M sodium phosphate (pH=7.8) for 16 hours, then against $H_2O$ (5×2 L). After lyophilization, 230 mg of the desired immunogen (11) was obtained.

EXAMPLE 3

SYNTHESIS OF IMIPRAMINE TRACER (12)

6-Carboxyfluorescein (1.00 g, 2.66 mmol) was dissolved in 8 mL DMF, 306 mg (2.66 mmol) of N-hydroxysuccinimide was added, 549 mg (2.66 mmol) of 1,3-dicyclohexylcarbo-diimide was added, and the reaction stirred for 17 hours, under $N_2$, in the dark. The reaction mixture was vacuum filtered, filtrate combined with 7.84 mg (2.65 mmol) of 2-aminoimipramine (4c), 0.56 mL (4.0 mmol) of triethylamine, and 4.0 mL DMF, and reaction allowed to stir 4 days under $N_2$, in the dark. Reaction solvents were removed in vacuo and residue purified on reverse phase C18 semi-preparative (1 mm) TLC plates, eluting with $H_2O$/THF/ HOAc (40/60/0.4) followed by preparative HPLC on a Waters mbondapak C18 column (19 mm× 150 mm), eluting with $H_2O$/THF/HOAc (35/65/0.4) at a flow rate of 7.0 mL/minute to yield 410 mg (24%) of the desired imipramine tracer (12) as an orange powder; mass spec (FAB) $(M+H)^+$ 654.

EXAMPLE 4

SYNTHESIS OF DESIPRAMINE TRACER (13)

6-Carboxyfluorescein (850 mg, 2.26 mmol) was dissolved in 10 mL DMF, 260 mg (2.26 mmol) of N-hydroxysuccinimide added, 466 mg (2.26 mmol) of 1,3-dicyclohexylcarbodiimide added, and solution stirred for 17 hours under $N_2$, in the dark. The reaction mixture was vacuum filtered, filtrate combined with 853 mg (2.24 mmol) of 2-amino desipramine derivative (9), 0.47 mL (3.4 mmol) of triethylamine and 4 mL DMF; the reaction was stirred for 4 days under $N_2$, in the dark. Solvents were removed in vacuo and residue purified first by column chromatography, eluting with $CH_2Cl_2$/MeOH (95/5), then $CH_2Cl_2$/MeOH (85/15), and then purified a second time on reverse phase C18 preparative (1 mm) TLC plates, eluting with $H_2O$/MeOH/ HOAc (10/90/0.4), to afford 510 mg (31%) of the intermediate BOC-protected, tracer as an orange powder; mass spec (FAB) $(M+H)^+740$.

The BOC-tracer (508 mg, 0.687 mmol) was combined with 7 mL $CH_2Cl_2$ and 7 mL trifluoroacetic acid, stirred 40 minutes, and solvent removed in vacuo. The residue was triturated twice with 20 mL aliquots of Hex/$CH_2Cl_2$ (1/1), then azeotroped 5 times with 20 mL aliquots of toluene/ MeOH (1/1), then left on a vacuum pump, in the dark, for 3 days to yield 599 mg of the desired desipramine tracer (13); mass spec (FAB) $(M+H)^+640$.

EXAMPLE 5

SYNTHESIS OF IMIPRAMINE SULFONAMIDE TRACER (14)

Triethylamine (0.03 mL, 0.20 mmol) was added to a solution of carboxylic acid (5b) (20 mg, 0.45 mmol), 2-ethyl-5-phenylisoxazolium-3'-sulfonate (Woodward's K, 13 mg, 0.0495 mmol) and 0.50 mL DMF; after stirring for 30 min under $N_2$, 4'-aminomethylfluorescein (AMF) hydrochlor-ide salt (18 mg, 0.045 mmol) and triethylamine (0.03 mL, 0.20 mmol) were added. The reaction was stirred for 18 hrs in the dark then solvents were removed in vacuo to give an orange solid which was purified on a reverse phase C18 preparative (1 mm) TLC plate, eluting with $H_2O$/MeOH/ HOAc (30/70/0.4), to afford 9.9 mg (28%) of the desired imipramine sulfonamide tracer (14). Mass spec (FAB) $(M+H)^+789$.

EXAMPLE 6

SYNTHESIS OF DESIPRAMINE SULFONAMIDE TRACER (15)

Triethylamine (0.03 mL, 0.20 mmol) was added to a solution of carboxylic acid (10b) (30 mg, 0.56 mmol), 2-ethyl-5-phenylisoxazolium-3'-sulfonate (Woodward's K, 16 mg, 0.062 mmol) and 0.50 mL DMF; after stirring for 30 min under $N_2$, 4'-aminomethylfluorescein (AMF) hydrochloride salt (22 mg, 0.056 mmol) and triethylamine (0.03 mL, 0.20 mmol) were added. The reaction was stirred for 21 hrs in the dark then solvents were removed in vacuo to give an orange solid which was purified on a silica gel preparative (2 mm) TLC plate, eluting with H$_2$O/MeOH/HOAc (30/70/0.4), to afford 49 mg (47%) of the desired intermediate BOC-protected tracer; mass spec (FAB) (M+H)$^+$825.

The BOC-tracer (23 mg, 0.026 mmol) was combined with 0.5 mL CH$_2$Cl$_2$ and 0.5 mL trifluoroacetic acid, stirred 5 minutes, and solvent removed in vacuo. Purification on a reverse phase C18 preparative (1 mm) TLC plate, eluting with H$_2$O/MeOH/HOAc (20/80/0.4) afforded 20 mg (99%) of the desired desipramine sulfonamide tracer (15); mass spec (FAB) (M+H)$^+$775.

EXAMPLE 7

ANTISERA PRODUCTION

Rabbits were initially immunized with 1 mg of immunogen and subsequently boosted with 0.5 mg of the immunogen until the response was mature (~12–15 weeks), after which the animals were boosted with 0.2 mg of the immunogen every 4 weeks. The animals were bled at 2 weeks and the bleeds were titrated to select antisera collections demonstrating adequate binding and displacement at a reasonable dilution. A typical pool for imipramine is diluted 1 to 250, has a binding of about 210 millipolarization units (mP) and a displacement of about 95 mP's with an imipramine solution containing 75 ng imipramine per milliliter; for desipramine a typical pool is diluted 1 to 250, has a binding of about 210 millipolarization nits and a displacement of about 95 mP's with an desipramine solution containing 75 ng desipramine per milliliter.

EXAMPLE 8

FLUORESCENCE POLARIZATION IMMUNOASSAY FOR IMIPRAMINE

Antisera was prepared by combining sera from 13 rabbits that had been immunized with the imipramine immunogen (6) as described in example 1. Individual titers among animals varied no more than 30% and all animals exhibited a mature immune response (6 months or greater on a single immunogen). The immunogen used was obtained from at least two separate synthetic preparations and gave equivalent response as judged by titer, avidity (curve characteristics), and cross-reactivity to desipramine (<10% at 50% deflection). The raw antisera were mixed and diluted into a buffer consisting of 0.100M glycylglycine, adjusted to pH 4.5 with 70% phosphoric acid. During the course of the assay the antisera was diluted in the Abbott TDx system with Abbott TDx system reagent buffer to a final concentration 1:16,000.

The fluorescent tracer (12) described in example 3 was prepared by diluting the dry reagent in a solution consisting of 25% dimethylforamide, 25% glycerol, and 50% distilled water in which was dissolved sufficient sodium chloride, and sodium thiosulfate, to result in concentrations of 1.0% and 0.1% respectively. This tracer reagent stock solution was then diluted to a concentration of ~40 nM in the same diluent matrix for use in the assay. During the course of the assay, this diluted tracer-preparation is further diluted with Abbott TDx system reagent buffer to a final concentration of ~480 pM.

Each test sample was prepared for analysis by means of an off-line multistep biphasic extraction procedure. To a 1.25 mL polypropylene test tube 0.100 mL of test sample was added. This test sample was then rendered basic by the addition of 0.100 mL of 0.25N sodium hydroxide and 0.025 mL of isoamyi-alcohol. This solution was mixed and allowed to stand at room temperature for 5 minutes. At the end of this period, 0.500 mL of n-decane was added to the sample followed by vortex mixing for 1.0 minute. After vortexing the sample was centrifuged for 5.0 minutes at ~8,000×g. At the end of this 5.0 minute centrifugation, 0.100 mL of the supernatant (upper phase) was removed to a second 1.25 mL polypropylene test tube containing 0.090 mL of 0.100M glycylglycine buffer (pH 3)/acetonitrile solution in a proportion of 9:1, respectively. At that point 0.010 mL of pretreatment solution (Z reagent=10 ug/mL solution of aqueous Chloramine-T) as described in pending U.S. patent application Ser. No. 627,282 (filed Dec. 14, 1990) and incorporated by reference herein. The solution was vortex mixed for 1.0 minute and between 0.050 and 0.100 mL of the lower phase from the second tube transferred to the sample well on an Abbott TDx analyzer.

The sample was run according to the standard protocol on the Abbott TDx analyzer in which the sample volume of 0.015 mL was combined with 0.025 mL of diluted antisera and 0.025 mL of diluted fluorescent tracer. The results at the termination of the assay run are expressed in millipolarization units (mP). The millipolarization units are automatically interpolated from a stored standard curve (FIG. 4) and expressed as concentration (ng/mL). Since the sample preparation procedure for the assay incorporates a 5-fold dilution of the sample, the gravimetric concentration of the calibrators from which the stored curve is constructed by a weighted four parameter curve fit are one fifth the expressed nominal concentration. The calibrators are prepared by gravimetric dilution in a buffer composed of 0.100M glycylglycine, pH 3. They are introduced into the Abbott TDx analyzer directly, without off-line sample treatment (biphasic extraction).

EXAMPLE 9

FLUORESCENCE POLARIZATION IMMUNOASSAY FOR DESIPRAMINE

Antisera was prepared by combining sera from 12 rabbits that had been immunized with the desipramine immunogen (11) as described in example 2. Individual titers among animals varied no more than 30% and all animals exhibited a mature immune response (6 months or greater on a single immunogen). The immunogen used was obtained from at least two separate synthetic preparations and gave equivalent response as judged by titer, avidity (curve characteristics), and crossreactivity to imipramine (<10% at 50% deflection). The raw antisera were mixed and diluted into a buffer consisting of 0.100M glycylglycine, adjusted to pH 4.5 with 70% phosphoric acid. During the course of the assay the antisera was diluted in the Abbott TDx system with Abbott TDx system reagent buffer to a final concentration 1:16,000.

The desipramine fluorescent tracer (13) described in example 4 was prepared by diluting the dry reagent in a solution consisting of 25% dimethylforamide, 25% glycerol, and 50% distilled water in which was dissolved sufficient sodium chloride, and sodium thiosulfate, to result in concentrations of 1.0% and 0.1% respectively. This tracer reagent stock solution was then diluted to a concentration of ~40 nM in the same diluent matrix for use in the assay. During the course of the assay, this diluted tracer preparation was further diluted with Abbott TDx system reagent buffer to a final concentration of ~480 pM.

Each test sample was prepared for analysis by means of an off-line multistep biphasic extraction procedure. To a 1.25 mL polypropylene test tube 0.100 mL of test sample was added. This test sample was then rendered basic by the addition of 0.100 mL of 0.25N sodium hydroxide and 0.025 mL of isoamyl-alcohol. This solution was mixed and allowed to stand at room temperature for 5 minutes. At the end of this period, 0.500 mL of n-decane was added to the sample followed by vortex mixing for 1.0 minute. After vortexing the sample was centrifuged for 5.0 minutes at ~8,000×g. At the end of this 5.0 minute centrifugation, 0.100 mL of the supernatant (upper phase) was removed to a second 1.25 mL polypropylene test tube containing 0.090 mL of 0.100M glyclyglycine buffer (pH 3)/acetonitrile solution in a proportion of 9:1, respectively. At that point 0.010 mL of pretreatment solution (Z reagent=10 ug/mL solution of aqueous Chloramine-T) as described in pending U.S. patent application Ser. No. 627,282 (filed Dec. 14, 1990) and incorporated by reference herein. The solution was vortex mixed for 1.0 minute and between 0.050 and 0.100 mL of the lower phase from the second tube was transferred to the sample well on an Abbott TDx analyzer.

The sample was run according to the standard protocol on the Abbott TDx analyzer in which the sample volume of 0.020 mL was combined with 0.025 mL of diluted antisera and 0.025 mL of diluted fluorescent tracer. The results at the termination of the assay run are expressed in millipolarization units (mP). The millipolarization units are automatically interpolated from a stored standard curve (FIG. 5) and expressed as concentration (ng/mL). Since the sample preparation procedure for the assay incorporates a 5-fold dilution of the sample, the gravimetric concentration of the calibrators from which the stored curve is constructed by a weighted four parameter curve fit are one fifth the expressed nominal concentration. The calibrators are prepared by gravimetric dilution in a buffer composed of 0.100M glycylglycine, pH 3. They are introduced into the Abbott TDx analyzer directly, without off line sample treatment (biphasic extraction).

EXAMPLE 10

EFFECT OF STRUCTURAL MODIFICATION OF THE IMIPRAMINE TRACER

Figure 4A:
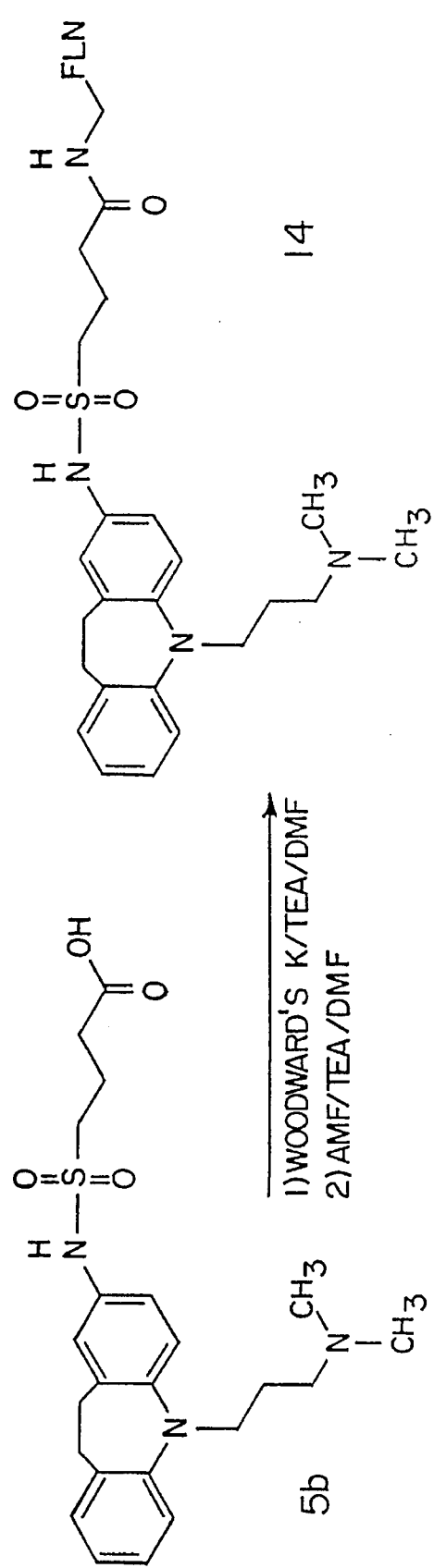
FIG. 4A illustrates the synthetic pathway for coupling imipramine to aminomethylfluorescein according to the method of the present invention and the structures of 4'-aminomethylfluorescein (HCl salt) and the 4'-fluoresceinyl substituent.
Figure 4A:
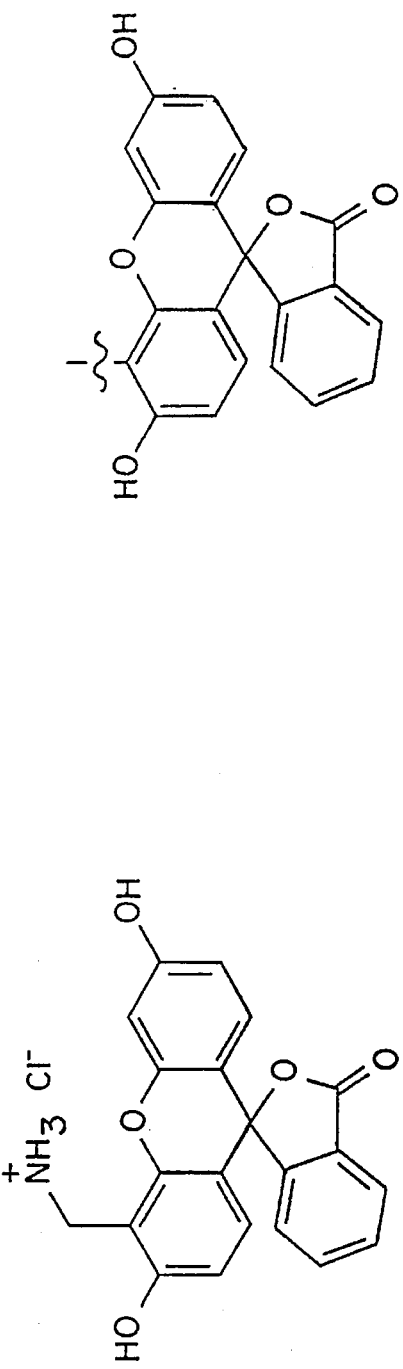
Figure 4B:
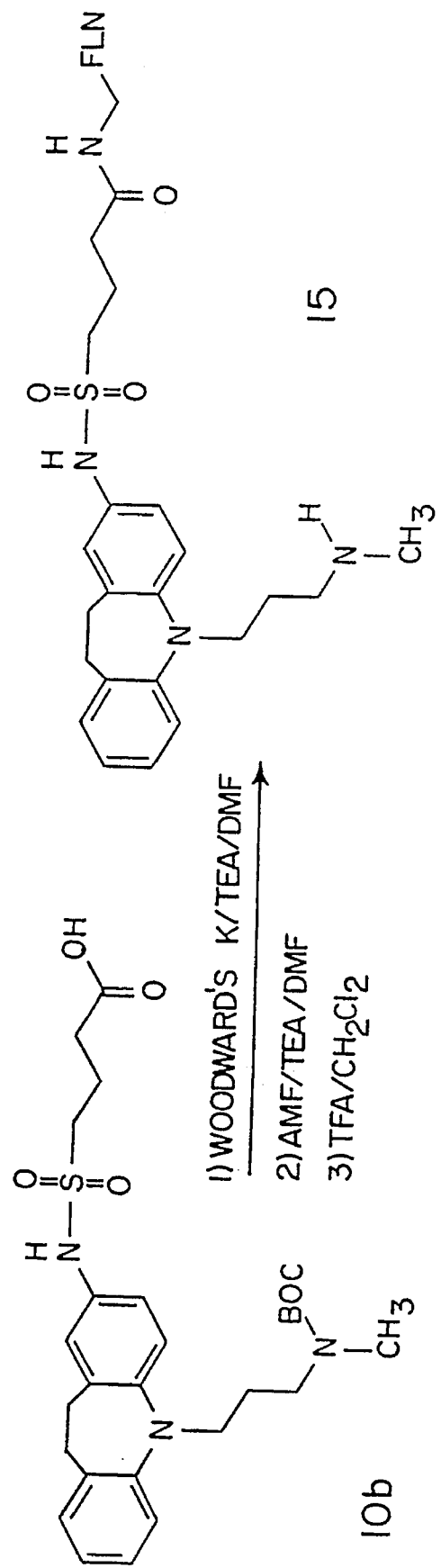
FIG. 4B illustrates the synthetic pathway for coupling desipramine to 4'-aminomethylfluorescein according to the method of the present invention.

Modification of the fluorescent tracer structure from a imipramine sulfonamide tracer (14), as shown in FIG. 4, to an imipramine amide tracer (12), as shown in FIG. 3, had a dramatic effect on assay characteristics. Calibration curves were generated from six known imipramine concentrations using the two fluorescent tracers (12) and (14) In the case of the tracer (14), which contained a sulfonamide linkage, displacement of the tracer by imipramine from the antibody-tracer complex is not efficient as shown by a flat curve and small span. Whereas in the case of tracer (12), which contained an amide linkage, excellent displacement of the tracer by imipramine from the antibody-tracer complex occurs as shown by a steep curve and a large span. The results are shown as graphs in FIG. 7. These findings illustrate a preferred embodiment of the present invention for a specific imipramine assay.

EXAMPLE 11

EFFECT OF STRUCTURAL MODIFICATION OF THE DESIPRAMINE TRACER

Figure 8:
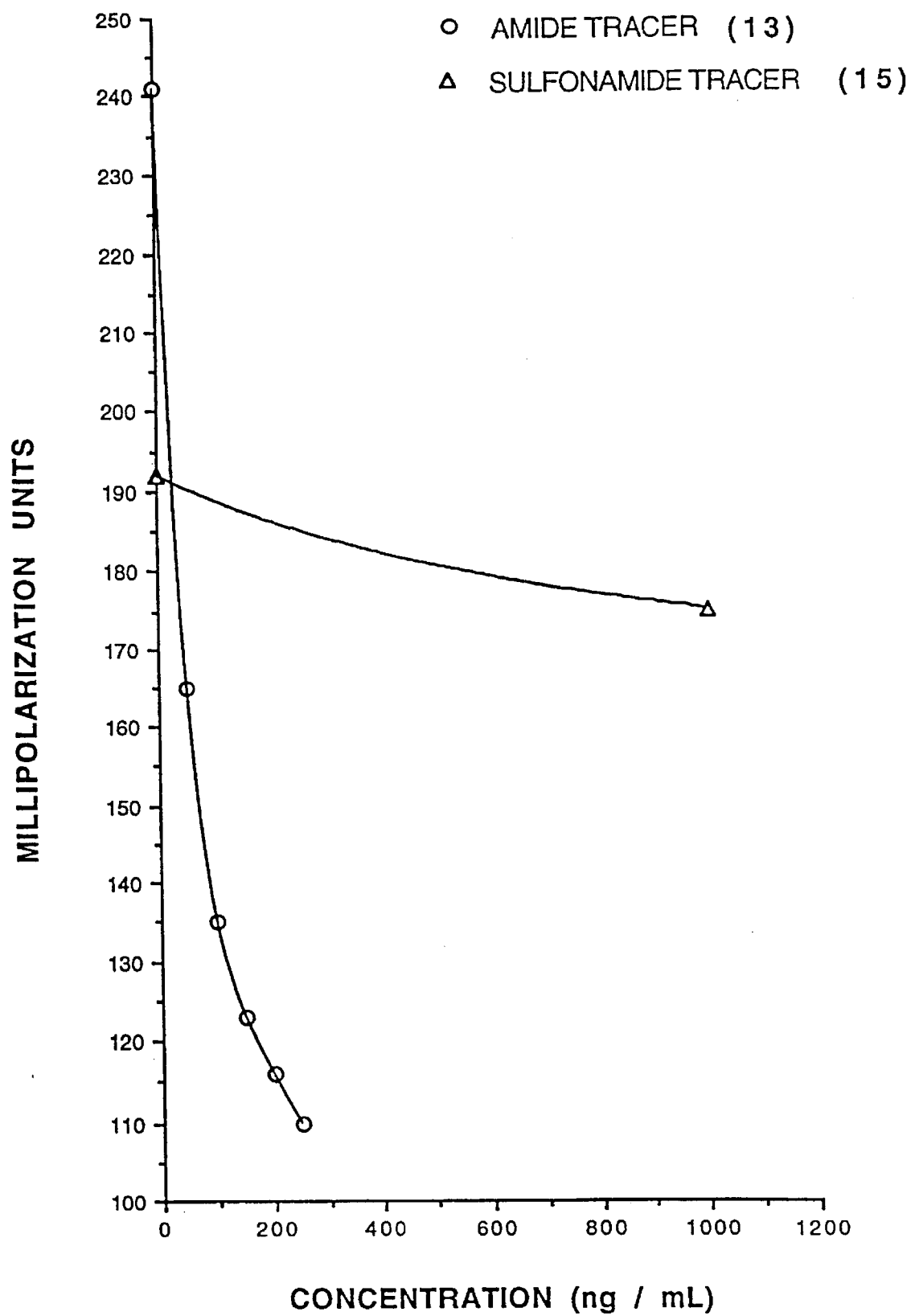
FIG. 8 is a graph which illustrates the effects of structural modification of a fluorescent tracer on a specific desipramine assay.

Modification of the fluorescent tracer structure from a desipramine sulfonamide tracer (15), as shown in FIG. 4, to a desipramiine amide tracer (13), as shown in FIG. 3, had a dramatic effect on assay characteristics. Calibration curves were generated from six known desipramine concentrations using the two fluorescent tracers (13) and (15) In the case of the tracer (15), which contained a sulfonamide linkage, displacement of the tracer by desipramine from the antibody-tracer complex is not efficient as shown by a flat curve and small span. Whereas in the case of tracer (13), which contained an amide linkage, excellent displacement of the tracer by desipramine from the antibody-tracer complex occurs as shown by a steep curve and a large span. The results shown as graphs in FIG. 8. These findings illustrate a preferred embodiment of the present invention for a specific desipramine assay.

EXAMPLE 12

DESCRIPTION OF HPLC METHOD AND COMPARATIVE ANALYSIS OF ABBOTT TDx IMIPRAMINE ASSAY VS. HPLC

The relative accuracy of the Abbott TDx imipramine assay was determined by correlation with HPLC analysis using patient sample extracts. The extracts for HPLC analysis were prepared as described below and the tricyclic antidepressant Trimipramine was used at a concentation of 4 ug/mL in acetonitrile as an internal standard.

1. Pipette 1.0 mL of patient standard into a 16×125 silylated tube fitted with a teflon screw cap. Remove the appropriate standard calibration curve frozen aliquots from the freezer and allow to thaw. Add 0.75 mL of acetonitrile containing the internal standard to each tube.
2. Add 1.0 mL of 0.25N NaOH followed by 0.200 mL of isoamyl alcohol, vortex vigorously, and allow the tubes to stand for 5.0 min.
3. Into each tube pipette 10.0 mL of n-heptane and tightly secure the cap of each tube. Shake the heptane/plasma biphasic mixture vigorously for 1.0 hour.
4. Remove the tubes from the shaker and transfer to the centrifuge. Centrifuge the heptane/plasma mixtures for 30 min at at least 2000×gravity(g) to clarify the layers.
5. Remove the tubes from the centrifuge and transfer the heptane upper layer to another silylated tube of the same description containing 1.0 mL of 0.1M, pH 3 glycylglycine buffer. Cap these tubes and shake vigorously for 1.0 hour.
6. Remove the tubes from the shaker and transfer to a centrifuge. Centrifuge the biphasic glycyl-glycine/heptane mixture for 30 min. at at least 2000×g.
7. Remove the tubes from the centrifuge, uncap and aspirate or pipette off the heptane upper layer and discard it.
8. Add 2.0 mL of 0.25N NaOH to each remaining glycylglycine lower phase. Add 5.0 mL of n-pentane to each aqueous extract, cap the tubes and shake for 1.0 hour.
9. Remove the tubes from the shaker and transfer to a centrifuge. Centrifuge the pentane/aqueous mixture at 200×g for 30 min.

10. Remove the tubes from the centrifuge and transfer the pentane upper layer to a 16×100 silylated conical screw top test tube. Place the caps on the test tubes tightly and unscrew ¼ turn. Place the tubes in a warm sand bath, transfer the sand bath containing the tubes to a vacuum desicator cabinet and apply the vacuum. Approximately 25–30 min is required for the pentane to evaporate.

11. Remove the tubes in the sand bath from the desicator and pipette into each tube 1.0 mL of pentane, recap and vortex each tube briefly. Open the caps ¼ turn and return the tubes to the desicator and reapply the vacuum for 10–15 min. until the pentane has evaporated.

12. Remove the dry tubes from the desicator and pipette in 0.070 mL of HPLC mobile phase. Vortex each tube for approx. 30 sec taking care to wet the tube sides.

13. Transfer the tubes to a centrifuge and centrifuge at 200×g for 2–3 min.

14. Remove the tubes from the centrifuge and transfer the entire contents to the WISP autocarousel sample cuvettes. The injection volume is set at 0.050 mL per injection onto a 10 cm.×0.6 cm. column packed with 3 micron silica with an 80 Angstrom pore size. The chromatographic mobile phase consisted of a mixture of 80 parts 0.025M dibasic sodium phosphate adjusted to pH 3 with concentrated phosphoric acid/20 parts acetonitrile/0.021M n-nonylamine (pH range=7.4–7.8). The analytical column is equipped with a dry packed guard column containing 40 micron pellicular silica. The solvent flow rate was 1.6 mL/min.

Linear regression analysis showed good correlation between the Abbott TDx Imipramine assay and the HPLC assay (N=102, R=0.9904, S=1.0153). The results are shown in FIG. 9.

EXAMPLE 13

COMPARATIVE ANALYSIS OF DESIPRAMINE TDx ASSAY VS. HPLC

Figure 10:
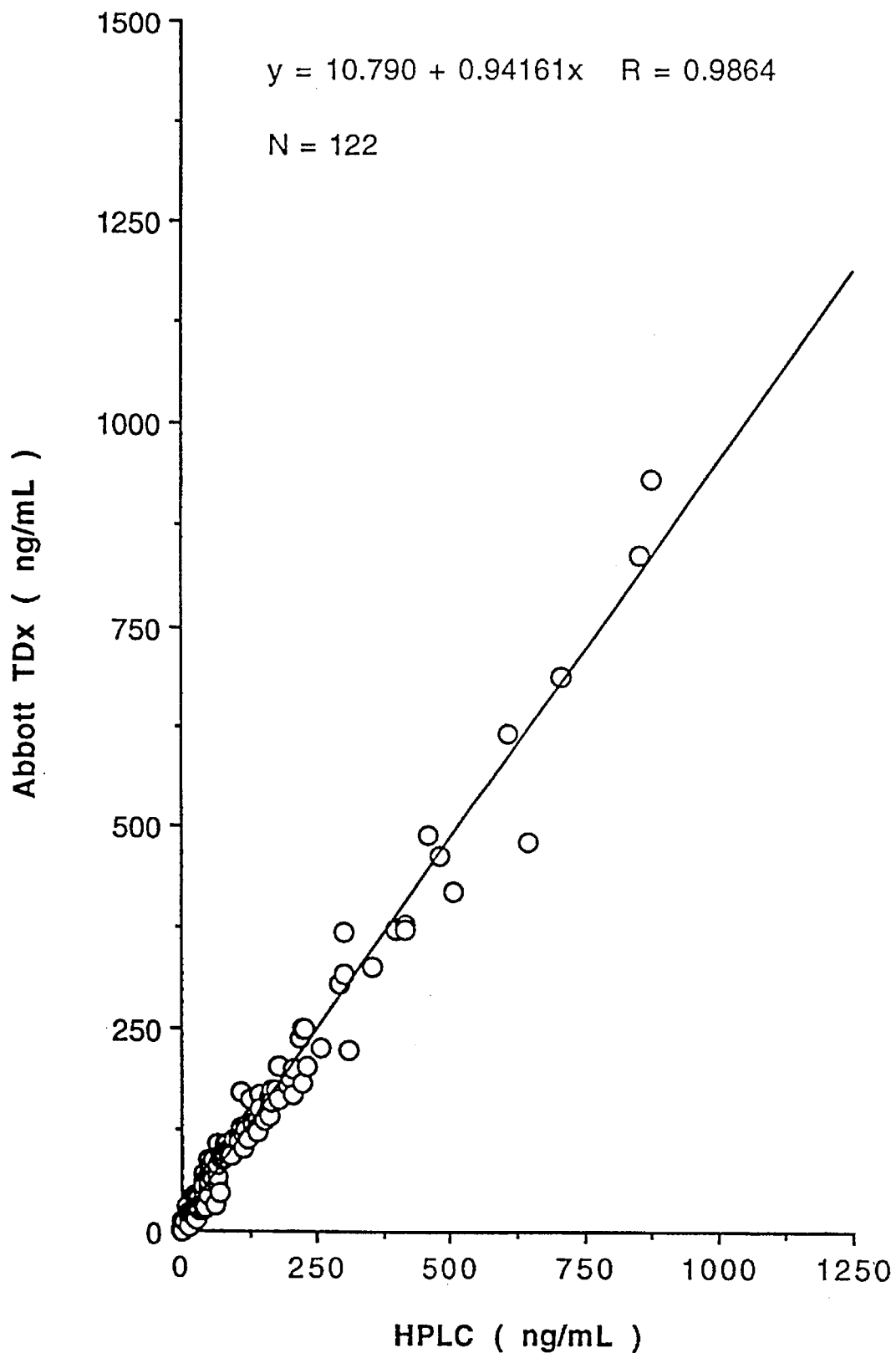
FIG. 10 is a graph which illustrates the accuracy of the method of fluorescence polarization immunoassay for the specific quantification of desipramine of the present invention compared to high performance liquid chromatography.

The relative accuracy of the Abbott TDx desipramine assay was determined by correlation with HPLC using patient sample extracts. The extracts for HPLC analysis were prepared and the chromatographic conditions used were the same as described above. Linear regression analysis showed good correlation between the Abbott TDx desipramine assay and the HPLC assay (N=122, R=0.9864, S=0.94161). The results are shown in FIG. 10.

It will be apparent that many modifications and variations of the present invention as herein set forth are possible without departing from the spirit and scope hereof, and that, accordingly, such limitations are imposed only as indicated by the appended claims.

We claim:

1. An antibody reagent comprising antibodies which are capable of binding to imipramine or desipramine in a test sample, wherein said antibodies are produced with an immunogen of an imipramine or desipramine derivative of the formula:

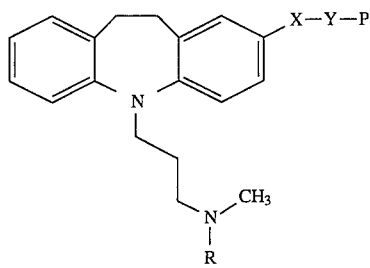

wherein X is —NH—SO$_2$—, Y is (CH$_2$)$_3$—CO—, R is CH$_3$ or H and P is an immunogenic carrier material.

2. The antibody reagent of claim 1 wherein for imipramine R of said immunogen is CH$_3$.

3. The antibody reagent of claim 1 wherein for desipramine R of said immunogen is H.

4. The antibody reagent of claim 1 wherein said immunogenic carrier material is selected from the group consisting of bovine serum albumin, keyhole limpet hemocyanin, and thyroglobulin.

5. A labeled reagent which is recognizable by antibodies capable of binding imipramine (when R$_1$ is —CH$_3$) or desipramine (when R$_1$ is —H) in a test sample, wherein said labeled reagent is an imipramine or desipramine derivative of the formula:

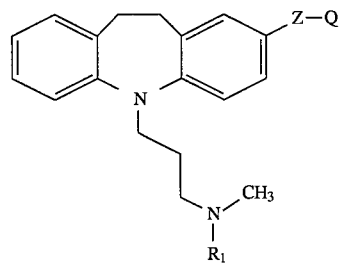

wherein Z is —NH—CO—, R$_1$ is CH$_3$ or H and Q is a detectable moiety.

6. The labeled reagent of claim 5 wherein for imipramine R$_1$ of said labeled reagent is CH$_3$.

7. The labeled reagent of claim 5 wherein for desipramine R$_1$ of said labeled reagent is H.

8. The labeled reagent of claim 5 wherein said detectable moiety is selected from the group consisting of enzymes, chromophores, fluorescent molecules, chemiluminescent molecules, phosphorescent molecules, and luminescent molecules.

9. The labeled reagent of claim 5 wherein said detectable moiety is a fluorescent molecule selected from the group consisting of aminomethylfluorescein, aminofluorescein, 5-fluoresceinyl, 6-fluoresceinyl, 5-carboxyfluorescein, 6-carboxyfluorescein, thioureafluorescein, and methoxytriazinolyl-aminofluorescein.

10. A labeled reagent which is recognizable by antibodies capable of binding imipramine or desipramine in a test sample, where said labeled reagent is an imipramine or desipramine derivative of the formula:

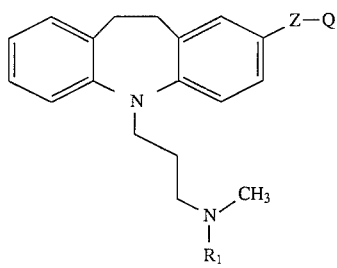

wherein Z is —NH—CO—, $R_1$ is $CH_3$ or H and Q is a fluorescent moiety.

11. The labeled reagent of claim 10 wherein for imipramine $R_1$ of said labeled reagent is $CH_3$.

12. The labeled reagent of claim 10 wherein for desipramine $R_1$ of said labeled reagent is H.

13. The labeled reagent of claim 10 wherein said fluorescent moiety is selected from the group consisting of aminomethylfluorescein, aminofluorescein, 5-fluoresceinyl, 6-fluoresceinyl, 5-carboxyfluorescein, 6-carboxyfluorescein, thioureafluorescein, and methoxytriazinolyl-aminofluorescein.

14. An immunogen of the formula:

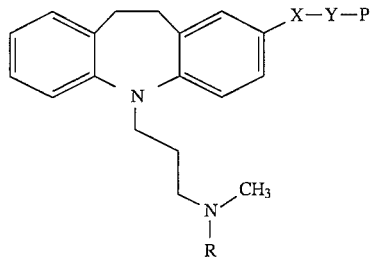

wherein X is —NH—$SO_2$—, Y is —$(CH_2)_3$—CO—, R is $CH_3$ or H and P is an immunogenic carrier material.

15. The immunogen of claim 14 wherein R is $CH_3$.

16. The immunogen of claim 14 wherein R is H.

17. The immunogen of claim 14 wherein said immunogenic carrier material is selected from the group consisting of bovine serum albumin, keyhole limpet hemocyanin, and thyroglobulin.

18. A compound of the formula:

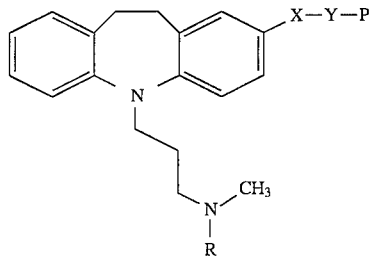

wherein R is $CH_3$, X is —NH—$SO_2$—, Y is —$(CH_2)_3$—CO—, and P is an immunogenic carrier material.

19. The compound of claim 18 wherein said immunogenic carrier material is selected from the group consisting of bovine serum albumin, thyroglobulin, and keyhole limpet hemocyanin.

20. The compound of claim 18 wherein X is —NH—$SO_2$—, Y is —$(CH_2)_3$—CO— and P is bovine serum albumin.

21. A compound of the formula:

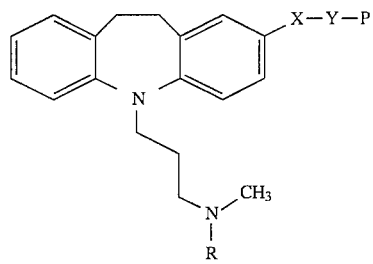

wherein R is H, X is —NH—$SO_2$—, Y is —$(CH_2)_3$—CO—, and P is an immunogenic carrier material.

22. The compound of claim 21 wherein said immunogenic carrier material is selected from the group consisting of bovine serum albumin, thyroglobulin, and keyhole limpet hemocyanin.

23. The compound of claim 21 wherein X is —NH—$SO_2$—, Y is —$(CH_2)_3$—CO— and P is bovine serum albumin.

24. A compound of the formula:

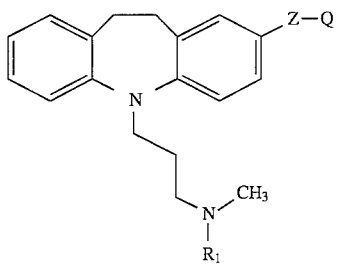

wherein $R_1$ is $CH_3$, Z is —NH—CO—, and Q is fluorescein or a fluorescein derivative.

25. The compound of claim 24 wherein said fluorescein or fluorescein derivative is selected from the group consisting of aminomethylfluorescein, aminofluorescein, 5-fluoresceinyl, 6-fluoresceinyl, 5-carboxyfluorescein, 6-carboxyfluorescein, thioureafluorescein, and methoxytriazinolyl-aminofluorescein.

26. The compound of claim 24 wherein Z is —NH—CO— and Q is 5-fluoresceinyl.

27. A compound of the formula:

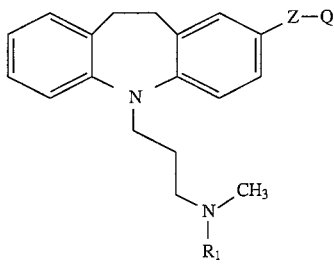

wherein $R_1$ is H, Z is —NH—CO—, and Q is fluorescein or a fluorescein derivative.

28. The compound of claim 27 wherein said fluorescein or fluorescein derivative is selected from the group consisting aminomethylfluorescein, aminofluorescein, 5-fluoresceinyl, 6-fluoresceinyl, 5-carboxyfluorescein, 6-carboxyfluorescein, thioureafluorescein, and methoxytriazinolyl-aminofluorescein.

29. The compound of claim 27 wherein Z is —NH—CO— and Q is 5-fluoresceinyl.

30. A test kit for the quantification of imipramine or desipramine in a test sample, said test kit comprising:

(a) an antibody reagent comprising antibodies which are capable of binding to imipramine or desipramine in a test sample, wherein said antibodies are produced with an immunogen of an imipramine or desipramine derivative of the formula:

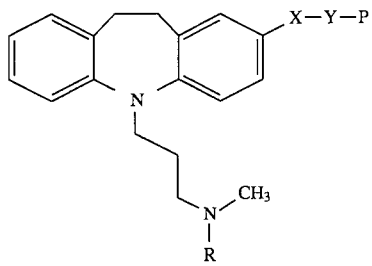

wherein X is —NH—SO$_2$—, Y is —(CH$_2$)$_3$—CO—, R is CH$_3$ or H and P is an immunogenic carrier material; and (b) a labeled reagent which is recognizable by antibodies capable of binding imipramine or desipramine in a test sample, wherein said labeled reagent is an imipramine or desipramine derivative of the formula:

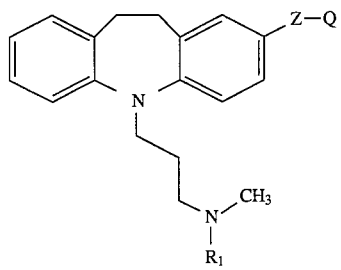

wherein Z is —NH—CO—, R$_1$ is CH$_3$ or H and Q is a fluorescent moiety.

31. The test kit of claim 30 for the quantification of imipramine wherein R of said immunogen is CH$_3$ and R$_1$ of said labeled reagent is CH$_3$.

32. The test kit of claim 30 for the quantification of desipramine wherein R of said immunogen is H and R$_1$ of said labeled reagent is H.

33. The test kit of claim 32 wherein said immunogenic carrier material is selected from the group consisting of bovine serum albumin, keyhole limpet hemocyanin, and thyroglobulin.

34. The test kit of claim 32 wherein said fluorescent moiety is selected from the group consisting of aminomethylfluorescein, amino-fluorescein, 5-fluoresceinyl, 6-fluoresceinyl, 5-carboxyfluorescein, 6-carboxyfluorescein, thioureafluorescein, and methoxytriazinolyl-aminofluorescein.

* * * * *

UNITED STATES PATENT AND TRADEMARK OFFICE
CERTIFICATE OF CORRECTION

PATENT NO. : 5,578,500
DATED : November 26, 1996
INVENTOR(S) : Adamczyk, et. Al.

It is certified that error appears in the above-indentified patent and that said Letters Patent is hereby corrected as shown below:

Column 9, line 50, change "CH2Cl$_2$" to --CH$_2$Cl$_2$--.

Column 11, line 7, change "(M+H)+382" to --(M+H)+382--.

Column 14, line 6, change "isoamyi-alcohol" to --isoamyl-alcohol--.

Column 17, line 64, change "imipraminc" to --imipramine--.

Column 22, line 20, change "claim 32" to --claim 30--.

Column 22, line 24, change "claim 32" to --claim 30--.

Signed and Sealed this

Twentieth Day of May, 1997

Attest:

BRUCE LEHMAN

Attesting Officer          Commissioner of Patents and Trademarks